US012799138B2

(12) United States Patent
Dolente et al.

(10) Patent No.: US 12,799,138 B2
(45) Date of Patent: Nov. 17, 2026

(54) THIADIAZOLOPYRIMIDONE DERIVATIVES

(71) Applicant: Hoffmann-La Roche Inc., Little Falls, NJ (US)

(72) Inventors: Cosimo Dolente, Allschwil (CH); Nadine Grether, Moehlin (CH); Fionn Susannah O'Hara, Basel (CH); Matilde Piras, Basel (CH); Hasane Ratni, Habsheim (FR); Michael Reutlinger, Freiburg (DE); Walter Vifian, Sissach (CH); Claudio Zambaldo, Basel (CH)

(73) Assignee: Hoffmann-La Roche Inc., Branchburg, NJ (US)

( * ) Notice: Subject to any disclaimer, the term of this patent is extended or adjusted under 35 U.S.C. 154(b) by 458 days.

(21) Appl. No.: 18/468,396

(22) Filed: Sep. 15, 2023

(65) Prior Publication Data

US 2024/0010659 A1 Jan. 11, 2024

Related U.S. Application Data

(63) Continuation of application No. PCT/EP2022/056587, filed on Mar. 15, 2022.

(30) Foreign Application Priority Data

Mar. 17, 2021 (EP) .................................... 21163263

(51) Int. Cl.
*C07D 519/00* (2006.01)
*A61P 25/28* (2006.01)

(52) U.S. Cl.
CPC ............ *C07D 519/00* (2013.01); *A61P 25/28* (2018.01)

(58) Field of Classification Search
CPC ............................... C07D 519/00; A61P 25/28
See application file for complete search history.

(56) References Cited

U.S. PATENT DOCUMENTS

| | | | | |
|---|---|---|---|---|
| 2020/0165256 A1 | 5/2020 | Woll et al. | | |
| 2024/0279239 A1* | 8/2024 | Reynolds | ............. | C07D 495/04 |

FOREIGN PATENT DOCUMENTS

| | | | |
|---|---|---|---|
| WO | 93/16050 A1 | 8/1993 | |
| WO | 94/00458 A1 | 1/1994 | |
| WO | 2013/057253 A1 | 4/2013 | |
| WO | 2013/119916 A2 | 8/2013 | |
| WO | 2015/048245 A1 | 4/2015 | |
| WO | 2015/173181 | 11/2015 | |
| WO | 2017/081111 A1 | 5/2017 | |
| WO | 2019/005980 | 1/2019 | |
| WO | 2019/005993 A1 | 1/2019 | |
| WO | 2019/057740 A1 | 3/2019 | |
| WO | 2020/005873 | 1/2020 | |
| WO | 2020/005877 | 1/2020 | |
| WO | 2020/005882 | 1/2020 | |
| WO | 2021/207530 | 10/2021 | |
| WO | 2021/207550 | 10/2021 | |
| WO | 2022/194800 | 9/2022 | |
| WO | 2022/194801 | 9/2022 | |
| WO | 2023/064879 | 4/2023 | |
| WO | 2023/170115 A1 | 9/2023 | |
| WO | 2023/225244 A1 | 11/2023 | |
| WO | 2024/218207 A1 | 10/2024 | |
| WO | 2025/111408 A1 | 5/2025 | |
| WO | 2026/087399 A1 | 4/2026 | |

OTHER PUBLICATIONS

"International Preliminary Report on Patentability—PCT/EP2022/056585" (Report Issuance Date: Sep. 12, 2023; Chapter I),:pp. 1-8 (Sep. 28, 2023).

"International Preliminary Report on Patentability—PCT/EP2022/056587" (Report Issuance Date: Sep. 12, 2023; Chapter I),:pp. 1-8 (Sep. 28, 2023).

International Preliminary Report on Patentability—PCT/EP2022/056586, (Report Issuance Date: Sep. 12, 2023; Chapter I),,:pp. 1-8 (Sep. 28, 2023).

"International Search Report—PCT/EP2022/056585" (w/Written Opinion),:pp. 1-12 (Jun. 24, 2022).

"International Search Report—PCT/EP2022/056587" (w/Written Opinion),:pp. 1-14 (May 27, 2022).

"International Search Report—PCT/EP2022/056586" (w/Written Opinion),:pp. 1-12 (May 25, 2022).

Lee, J., et al., "Huntington's disease onset is determined by length of uninterrupted CAG, not encoded polyglutamine, and is modified by DNA maintenance mechanisms" Biorxiv—Cold Spring Harbor Lab 529768:1-72 (Jan. 24, 2019).

Tabrizi, S., et al., "Huntingtin Lowering Strategies for Disease Modification in Huntington's Disease" Neuron—Cell Press 101(5):801-819 (Mar. 6, 2019).

Tabrizi, S., et al., "Potential endpoints for clinical trials in premanifest and early Huntington's disease in the TRACK-HD study: analysis of 24 month observational data" Lancet Neurol (Epub: Dec. 2, 2011), 11(01):42-53 (Jan. 1, 2012).

(Continued)

*Primary Examiner* — Erich A Leeser
(74) *Attorney, Agent, or Firm* — Robert C. Hall; Genentech, Inc.

(57) ABSTRACT

The invention relates to a compound of formula (I)

(I)

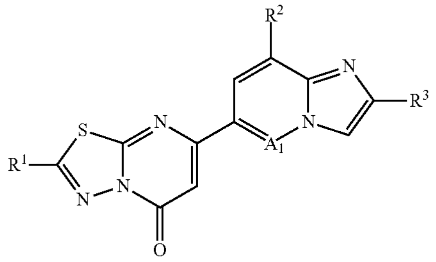

wherein $R^1$-$R^4$ and $A_1$ are as defined in the description and in the claims. The compound of formula (I) can be used as a medicament.

15 Claims, No Drawings

(56) References Cited

OTHER PUBLICATIONS

Wang, N., et al., "Neuronal targets for reducing mutant huntingtin expression to ameliorate disease in a mouse model of Huntington's disease" Nature Med (Epub: Apr. 28, 2014), 20(5):536-541 (May 1, 2014).
Wild, E., et al., "Therapies targeting DNA and RNA in Huntington's disease" Lancet Neurol 16(10):837-847 (Oct. 1, 2017).
Brighty, K.E et al., "Synthesis of (1β,5α,6α)-6-Amino-3-azabicyclo[3.1.0]hexane, a Novel Achiral Diamine" Synlett 11:pp. 1097-1099 (Nov. 1996).
CAS Registry Database, 2726461-18-1, (7-(8-Fluoro-2-methylimidazo[1,2-a]pyridin-6-yl)-2-(4-methyl-1-piperazinyl)-5H-1,3,4-thiadiazolo[3,2-a]pyrimidin-5-one), pp. 1 Nov. 7, 2021.
CAS Registry Database, 2726461-23-8, (2-(4,7-diazaspiro[2.5]oct-7-yl)-7-(8-fluoro-2-methylimidazo[1,2-a]pyridin-6-yl)-5H-1,3,4-Thiadiazolo[3,2-a]pyrimidin-5-one), pp. 1 Nov. 7, 2021.
CAS Registry Database, 2726462-68-4, (7-(8-Fluoro-2-methylimidazo[1,2-a]pyridin-6-yl)-2-(1-methyl-4-piperidinyl)-5H-1,3,4-thiadiazolo[3,2-a]pyrimidin-5-one), pp. 1 Nov. 7, 2021.
CAS Registry Database, 2726462-72-0, (7-(8-Fluoro-2-methylimidazo[1,2-a]pyridin-6-yl)-2-(4-piperidinyl)-5H-1,3,4-thiadiazolo[3,2-a]pyrimidin-5-one), pp. 1 Nov. 7, 2021.
CAS Registry Database, 2726462-78-6, (7-(8-Fluoro-2-methylimidazo[1,2-a]pyridin-6-yl)-2-(1-piperazinyl)-5H-1,3,4-thiadiazolo[3,2-a]pyrimidin-5-one), pp. 1 Nov. 7, 2021.
CAS Registry Database, 2839514-70-2, (7-(8-Fluoro-2-methylimidazo[1,2-b]pyridazin-6-yl)-2-(4-piperidinyl)-5H-1,3,4-thiadiazolo[3,2-a]pyrimidin-5-one), pp. 1 Oct. 13, 2022.
CAS Registry Database, 2923320-28-7, (7-(8-fluoro-2-methylimidazo[1,2-a]pyridin-6-yl)-2-(2,2,6,6-tetramethyl-4-piperidinyl)-5H-1,3,4-Thiadiazolo[3,2-a]pyrimidin-5-one), pp. 1 May 11, 2023.
Frances et al., "Developing Splice Modifier Therapies at Roche: Learnings and Challenges" European Federation for Medicinal Chemistry—10th International Symposium on Advances in Synthetic and Medicinal Chemistry:pp. 1 (Sep. 1, 2025).
International Preliminary Report on Patentability—PCT/EP2023/055838 issued Sep. 10, 2024, pp. 1-9.
"International Preliminary Report on Patentability—PCT/EP2024/060533":pp. 1-7 (Oct. 16, 2025).
"International Search Report—PCT/EP2025/080143" (w/Written Opinion),:pp. 1-12 (Dec. 4, 2025).
"International Search Report—PCT/EP2024/060533" (w/Written Opinion),:pp. 1-10 (Jul. 5, 2024).
International Search Report with Written Opinion—PCT/EP2023/055838 mailed Apr. 26, 2023, pp. 1-15.
Jang, M.-Y. et al., "Synthesis, immunosuppressive activity and structure-activity relationship study of a new series of 4-N-piperazinyl-thieno[2,3-d]pyrimidine analogues" Bioorganic & Medicinal Chemistry Letters 20(3):844-847 ( 2010).
Katritzky, A.R. et al., "The preparation and fungicidal activity of a series of thiazolyl- and isothiazolyl-diarylcarbinols" Can. J. Chem. 66(7):pp. 1617-1628 (Jul. 1988) https://doi.org/10.1139/v88-262.
Sanchez et al., "Huntington's Disease: Mechanisms of Pathogenesis and Therapeutic Strategies" Cold Spring Harbor Perspectives in Medicine 7:pp. 1-22 ( 2017) DOI: 10.1101/cshperspect.a024240.

* cited by examiner

THIADIAZOLOPYRIMIDONE DERIVATIVES

This application is a Continuation of International Application No. PCT/EP2022/056587, filed 15 Mar. 2022, which claims benefit of European Patent Application No. 21163263.3, filed 17 Mar. 2021, each of which is incorporated herein by reference in its entirety and for all purposes.

The present invention relates to new organic compounds useful for therapy and/or prophylaxis in a mammal, and in particular to compounds that reduce the protein level of huntingtin (HTT) and which are useful in the treatment of Huntington's disease.

In particular, the present invention relates to a compound of formula (I)

(I)

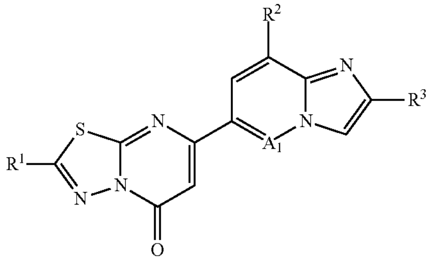

wherein $R^1$ is hydrogen, alkyl, cycloalkyl, aryl, heteroaryl or heterocycloalkyl, wherein each instance of cycloalkyl, aryl, heteroaryl and heterocycloalkyl is optionally substituted with one, two, three or four substituents independently selected from $R^4$;

$R^2$ is hydrogen, cycloalkyl, alkenyl, cyano, amino, hydroxyl, halogen, alkyl, haloalkyl, haloalkoxy or alkoxy;

$R^3$ is alkyl, alkoxy, hydrogen, halogen or haloalkyl;

$R^4$ is halogen, alkyl, heterocycloalkyl, heterocycloalkylalkyl, alkylheterocycloalkyl, haloheterocycloalkyl, cycloalkyl, cycloalkylalkyl, alkylcycloalkyl, halocycloalkyl, cycloalkylamino, aryl, arylalkyl, alkylaryl, haloaryl, cyano, hydroxy, oxo, haloalkyl, alkylcarbonyl, alkoxy, haloalkoxy, alkoxyalkyl, alkoxycarbonyl, amino, alkylamino, dialkylamino, aminoalkyl, alkylaminoalkyl, dialkylaminoalkyl, aminoalkylamino, alkoxyalkylamino, alkylcarbonylamino, alkoxycarbonylamino, hydroxyalkyl, hydroxyalkoxyalkyl or hydroxyalkylamino; and $A_1$ is —CH— or —N—;

or a pharmaceutically acceptable salt thereof;

provided that 7-(8-fluoro-2-methyl-imidazo[1,2-a]pyridin-6-yl)-2-(1-methyl-4-piperidyl)-[1,3,4]thiadiazolo[3,2-a]pyrimidin-5-one;

7-(8-fluoro-2-methyl-imidazo[1,2-a]pyridin-6-yl)-2-(4-piperidyl)[1,3,4]thiadiazolo[3,2-a]pyrimidin-5-one;

7-(8-fluoro-2-methyl-imidazo[1,2-a]pyridin-6-yl)-2-(4-methylpiperazin-1-yl)-[1,3,4]thiadiazolo[3,2-a]pyrimidin-5-one;

7-(8-fluoro-2-methyl-imidazo[1,2-a]pyridin-6-yl)-2-piperazin-1-yl-[1,3,4]thiadiazolo[3,2-a]pyrimidin-5-one;

7-(8-fluoro-2-methyl-imidazo[1,2-a]pyridin-6-yl)-2-(2,2,6,6-tetramethyl-4-piperidyl)-[1,3,4]thiadiazolo[3,2-a]pyrimidin-5-one; and 2-(4,7-diazaspiro[2.5]octan-7-yl)-7-(8-fluoro-2-methyl-imidazo[1,2-a]pyridin-6-yl)-[1,3,4]thiadiazolo[3,2-a]pyrimidin-5-one;

are excluded.

Huntington's Disease (HD) is an inherited autosomal dominant neurodegenerative disease caused due to a CAG bases repeat expansion in the huntingtin (HTT) gene. Several lines of evidence indicate that the mutant HTT gene together with its gene product mHTT protein contributes to HD pathogenesis via a toxic gain of function mechanism.

The triplet repeat expansion in the exon 1 of the HTT gene translates into a polyglutamine repeat in the HTT protein which is prone to misfolding and aggregating in the cells. While the exact mechanisms of how mutant HTT disrupts cellular function is unclear, several processes ranging from interruption of RNA translation, toxic RNA species, protein aggregates, RNA translation, and stress granules have been implicated.

At a neural circuit level, HD has been shown to affects deep brains structures like the striatum as well as cortical regions to different extents. Seminal mouse genetic experiments coupled with human imaging experiments point to a key role of cortico-striatal connections in the pathogenicity of HD (Wang et al., "Neuronal targets of mutant huntingtin genetic reduction to ameliorate Huntington's disease pathogenesis in mice" Nature medicine 20.5 (2014): 536; Tabrizi et al.; "Potential endpoints for clinical trials in premanifest and early Huntington's disease in the TRACK-HD study: analysis of 24 month observational data." The Lancet Neurology 11.1 (2012): 42-53).

HD typically manifests around 30-50 years of age characterized by a multitude of symptoms spanning the motor, cognitive and affective domains eventually leading to death in years after the onset of motor symptoms. CAG repeat length negatively correlates with age of onset of motor symptoms, however this only accounts for 50-70% of the variance in age of onset. In an effort to identify genetic modifiers of age of onset in HD, Lee et al. (2019, Huntington's disease onset is determined by length of uninterrupted CAG, not encoded polyglutamine, and is modified by DNA maintenance mechanisms. Bioarxiv doi: https://doi.org/10.1101/529768) conducted a large GWAS (genome-wide association study) that has uncovered additional genetic modifiers of age of onset.

Various mouse models have been characterized to model aspects of HD. The YAC128 mice expressing the full length mutant HTT transgene with 128 CAG repeats, BACHD mice expressing the full length mutant HTT genomic sequence with 97 CAG/CAA repeats, the R6/2 mice expressing exon 1 of the mutant human HTT gene with 110-135 CAG repeats). In addition to these mice that express the human transgene, there are also a series of mouse models, like the frequently used Q111, the Q175 knock in mice where the expanded repeats are knocked-in in the context of the mouse HTT locus.

There are currently no disease modifying therapies for Huntington's Disease while several are in development. The core disease process behind the symptomatology characterized by motor, cognitive and behavioral symptoms remains unmet by the various symptomatic treatments currently approved. Tetrabenazine and tiapride are currently approved for the treatment of motor symptoms namely HD-associated chorea. In addition, anticonvulsants, benzodiazepines, antidepressants, and antipsychotics are also used off-label to treat the motor, cognitive and psychiatric symptoms associated with HD.

Several therapeutic strategies targeting DNA and RNA are being investigated for HTT lowering (E. J. Wild, S. Tabrizi, Lancet Neurol. 2017 16(10): 837-847). HTT lowering is a promising therapeutic approach that aims to slow disease progression by getting at the core cause of Huntington's Disease. HTT lowering is thought to be transformative when treated in the pre-manifest or manifest stages of disease onset, thus preventing major neurodegenerative processes in the brain. However, the challenge lies in identifying the patients at the right disease stage, as age of onset is quite variable across the population (S. J. Tabrizi, R. Ghosh, B. R. Leavitt, Neuron, 2019, 102(4), 899).

The current clinical approaches are mainly based on antisense oligonucleotides (ASOs). In addition, a few allele specific lowering strategies such as SNP (single-nucleotide polymorphism) based ASO and zinc finger based gene editing approaches are investigated. While the use of small molecules to lower HTT expression has been postulated, this strategy has not yet been validated and none has proved successful so far.

Small molecules provide an opportunity to allow for HTT lowering in the brain as well as the periphery. In addition, a small molecule modality allows access to patient populations that could be difficult to reach with modalities like ASOs or gene therapy.

There is thus the need for new compounds capable of lowering mHTT.

The applicant has surprisingly found that the compounds of the invention are active in lowering mHTT and are therefore useful in the treatment of HD.

All publications, patent applications, patents, and other references mentioned herein are incorporated by reference in their entirety.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls. Particular examples of "alkyl" are methyl, ethyl and isopropyl. Methyl is a particular example of "alkyl" in the compound of formula (I).

In the present description the term "alkenyl", alone or in combination, signifies a straight-chain or branched-chain alkenyl group with 2 to 8 carbon atoms and further comprising at least one double bond, particularly a straight or branched-chain alkenyl group with 2 to 4 carbon atoms and further comprising at least one double bond. Particular examples of "alkenyl" are ethenyl, propenyl, isopropenyl, butenyl, isobutenyl and tertbutenyl. Isopropenyl is a particular example of "alkenyl" in the compound of formula (I).

The term "cycloalkyl", alone or in combination, signifies a cycloalkyl ring with 3 to 10 carbon atoms and particularly a cycloalkyl ring with 3 to 6 carbon atoms. Examples of "cycloalkyl" are cyclopropyl, cyclobutyl, cyclopentyl and cyclohexyl, cycloheptyl, cyclooctyl, cyclononyl and cyclodecyl. A particular example of "cycloalkyl" is cyclopropyl.

The term "aryl", alone or in combination, signifies an aromatic mono- or bicyclic ring system comprising 6 to 10 carbon ring atoms. Examples of "aryl" include, but are not limited to, phenyl and naphthyl.

The term "heteroaryl", alone or in combination, signifies an aromatic mono- or bicyclic ring system with 5 to 12 ring atoms, comprising 1, 2, 3 or 4 heteroatoms each independently selected from N, O and S, the remaining ring atoms being carbon. Examples of heteroaryl include, but are not limited to, furanyl, thiophenyl, 1H-pyrazolyl, 1H-imidazolyl, 1H-1,2,3-triazolyl, 4H-1,2,4-triazolyl, 1,2,4-oxadiazolyl, 1,3,4-oxadiazolyl, pyridinyl, pyridazinyl, pyrimidinyl, pyrazinyl, 1H-indolyl, 2H-indolyl, 1H-indazolyl, 2H-indazolyl, indolizinyl, benzofuranyl, 1H-b enzimidazolyl, 1,3-benzoxazolyl, furo[2,3-b]pyridinyl, furo[2,3-c]pyridinyl, furo[3,2-b]pyridinyl, furo[3,2-c]pyridinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, 1H-pyrazolo[4,3-b]pyridinyl, 2H-pyrazolo[4,3-b]pyridinyl, 2H-pyrazolo[4,3-c]pyridinyl, pyrazolo[1,5-a]pyrazinyl, pyrazolo[1,5-a]pyrimidinyl, imidazo[1,2-a]pyridinyl, imidazo[1,2-a]pyrimidinyl, imidazo[1,2-a]pyrazinyl, imidazo[1,2-b]pyridazinyl, imidazo[1,2-c]pyrimidinyl, imidazo[1,5-a]pyridinyl, imidazo[2,1-b][1,3]thiazolyl, imidazo[2,1-b][1,3,4]thiadiazolyl, [1,3]oxazolo[4,5-b]pyridinyl, [1,2,4]triazolo[1,5-a]pyridnyl, [1,2,4]triazolo[1,5-b]pyridazinyl, benzo[d]oxazolyl and quinolinyl.

The term "alkoxy" or "alkyloxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy.

The term "oxy", alone or in combination, signifies the —O— group.

The terms "halogen" or "halo", alone or in combination, signifies fluorine, chlorine, bromine or iodine and particularly fluorine, chlorine or bromine. A particular example of halogen is fluorine. The term "halo", in combination with another group, if not otherwise specified, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Particular "haloalkyl" are fluoromethyl, trifluoromethyl, difluoromethyl, fluoroethyl, fluoropropyl and fluorobutyl. A particular example of "haloalkyl" is trifluoromethyl.

The term "haloalkoxy", alone or in combination, denotes an alkoxy group substituted with at least one halogen, particularly substituted with one to five halogens, particularly one to three halogens. Particular "haloalkoxy" are fluoromethoxy, fluoroethoxy, difluoromethoxy, difluoroethoxy, trifluoromethoxy and trifluoroethoxy.

The terms "hydroxyl" and "hydroxy", alone or in combination, signify the —OH group.

The term "cyano", alone or in combination, signifies the —CN group.

The term "carbonyl", alone or in combination, signifies the —C(O)— group.

The term "oxo", alone or in combination, signifies the =O group.

The term "amino", alone or in combination, signifies the primary amino group (—$NH_2$), the secondary amino group (—NH—), or the tertiary amino group (—N—).

The term "alkylamino", alone or in combination, signifies an alkyl group linked to a —NH—group. The term "dialkylamino", alone or in combination, signifies two alkyl groups linked to a —N— atom.

The term "cyano", alone or in combination, signifies the —CN group.

The term "heterocycloalkyl", alone or in combination, signifies a monocyclic or bicyclic saturated or monounsaturated ring system with 3 to 12 ring atoms, comprising 1, 2, 3 or 4 heteroatoms each independently selected from N, O and S, and the remaining ring atoms being carbon. In some particular embodiments the term "heterocycloalkyl", alone or in combination, can signify a monocyclic or bicyclic saturated or monounsaturated ring system with 5 to 10 ring atoms, comprising 1 or 2 nitrogen atoms and the remaining ring atoms being carbon. Examples of "heterocycloalkyl" are piperazinyl, azetidinyl, morpholinyl, tetrahydropyranyl, tetrahydrofuranyl, 1,2,3,6-tetrahydropyridin-4-yl, 4,7-diazaspiro[2.5]octan-7-yl, (8aS)-3,4,6,7,8,8a-hexahydro-1H-pyrrolo[1,2-a]pyrazin-2-yl, (8aR)-3,4,6,7,8,8a-hexahydro-1H-pyrrolo[1,2-a]pyrazin-2-yl, 3,8-diazabicyclo[3.2.1]octan-8-yl, (I S,4S)-2,5-diazabicyclo[2.2.1]heptan-2-yl, 2,3,3a,4,6,6a-hexahydro-1H-pyrrolo[3,4-c]pyrrol-5-yl, pyrrolidinyl, 2,8-diazaspiro[4.5]decan-2-yl, piperidyl, (7R)-4-azaspiro[2.5]octan-7-yl, (75)-4-azaspiro[2.5]octan-7-yl and 4-azaspiro[2.5]octan-7-yl. Particular examples of "heterocycloalkyl" are 2-piperazinyl, 4-piperidyl, pyrrolidin-3-yl, (8aS)-3,4,6,7,8,8a-hexahydro-1H-pyrrolo[1,2-a]pyrazin-2-yl, 4,7-diazaspiro[2.5]octan-7-yl and 4-azaspiro[2.5]octan-7-yl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and trifluoroacetic acid. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts formed with trifluoroacetic acid or hydrochloric acid.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz). A particular example of a protecting group is tert-butoxycarbonyl (Boc).

A certain embodiment of the invention relates to the compound of formula (I) as described herein, or a pharmaceutically acceptable salt thereof, wherein at least one substituent comprises at least one radioisotope. Particular examples of radioisotopes are $^2H$, $^3H$, $^{13}C$, $^{14}C$ and $^{18}F$.

Furthermore, the invention includes all optical isomers, i.e. diastereoisomers, diastereomeric mixtures, racemic mixtures, all their corresponding enantiomers and/or tautomers as well as their solvates, wherever applicable, of the compound of formula (I).

The compound of formula (I) may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

The term "asymmetric carbon atom" means a carbon atom with four different substituents. According to the Cahn-Ingold-Prelog Convention an asymmetric carbon atom can be of the "R" or "S" configuration.

The invention thus also relates in particular to:

A compound according to the invention wherein $R^1$ is heterocylcoalkyl optionally substituted with one, two, three or four substituents independently selected from $R^4$;

A compound according to the invention wherein $R^1$ is heterocylcoalkyl optionally substituted with one or two independently selected from $R^4$;

A compound according to the invention wherein $R^1$ is 2-piperazinyl, 4-piperidyl, pyrrolidin-3-yl, (8a S)-3,4,6,7,8,8a-hexahydro-1H-pyrrolo[1,2-a]pyrazin-2-yl, 4,7-diazaspiro[2.5]octan-7-yl or 4-azaspiro[2.5]octan-7-yl, and wherein $R^1$ is optionally substituted with one or two substituents independently selected from $R^4$;

A compound according to the invention wherein $R^1$ is 4-piperidyl or 4-azaspiro[2.5]octan-7-yl, and wherein $R^1$ is optionally substituted with one or two substituents independently selected from $R^4$;

A compound according to the invention wherein $R^2$ is halogen, alkyl or haloalkyl;

A compound according to the invention wherein $R^2$ is fluoro, methyl or trifluoromethyl;

A compound according to the invention wherein $R^3$ is alkyl;

A compound according to the invention wherein $R^3$ is methyl;

A compound according to the invention wherein $R^4$ is halogen or alkyl;

A compound according to the invention wherein $R^4$ is fluoro or methyl;

A compound according to the invention wherein $A_1$ is —N—; and

A compound according to the invention wherein $A_1$ is —CH—.

The invention further relates to a compound selected from 7-(2,8-dimethylimidazo[1,2-b]pyridazin-6-yl)-2-piperazino-[1,3,4]thiadiazolo[3,2-a]pyrimidin-5-one;

7-(2,8-dimethylimidazo[1,2-b]pyridazin-6-yl)-2-(4-piperidyl)-[1,3,4]thiadiazolo[3,2-a]pyrimidin-5-one;

7-(2,8-dimethylimidazo[1,2-b]pyridazin-6-yl)-2-[(3R,5S)-3,5-dimethylpiperazin-1-yl]-[1,3,4]thiadiazolo[3,2-a]pyrimidin-5-one;

2-[(8aS)-3,4,6,7,8,8a-hexahydro-1H-pyrrolo[1,2-a]pyrazin-2-yl]-7-(2,8-dimethylimidazo[1,2-b]pyridazin-6-yl)-[1,3,4]thiadiazolo[3,2-a]pyrimidin-5-one;

2-(4,7-diazaspiro[2.5]octan-7-yl)-7-(2,8-dimethylimidazo[1,2-b]pyridazin-6-yl)-[1,3,4]thiadiazolo[3,2-a]pyrimidin-5-one;

2-(4-azaspiro[2.5]octan-7-yl)-7-(2,8-dimethylimidazo[1,2-b]pyridazin-6-yl)-[1,3,4]thiadiazolo[3,2-a]pyrimidin-5-one;

7-(2,8-dimethylimidazo[1,2-b]pyridazin-6-yl)-2-(4-fluoro-4-piperidyl)-[1,3,4]thiadiazolo[3,2-a]pyrimidin-5-one;

7-[2-methyl-8-(trifluoromethyl)imidazo[1,2-b]pyridazin-6-yl]-2-(4-piperidyl)-[1,3,4]thiadiazolo[3,2-a]pyrimidin-5-one; and 7-(2,8-dimethylimidazo[1,2-b]pyridazin-6-yl)-2-pyrrolidin-3-yl-[1,3,4]thiadiazolo[3,2-a]pyrimidin-5-one;

or a pharmaceutically acceptable salt thereof.

The invention further relates to a compound selected from 7-(2,8-dimethylimidazo[1,2-b]pyridazin-6-yl)-2-(4-piperidyl)-[1,3,4]thiadiazolo[3,2-a]pyrimidin-5-one;

2-(4-azaspiro[2.5]octan-7-yl)-7-(2,8-dimethylimidazo[1,2-b]pyridazin-6-yl)-[1,3,4]thiadiazolo[3,2-a]pyrimidin-5-one; and 7-(2,8-dimethylimidazo[1,2-b]pyridazin-6-yl)-2-(4-fluoro-4-piperidyl)-[1,3,4]thiadiazolo[3,2-a]pyrimidin-5-one;

or a pharmaceutically acceptable salt thereof.

The synthesis of the compound of formula (I) can, for example, be accomplished according to the following schemes. X, $R^1$-$R^4$ and $A_1$ are as defined above, unless otherwise specified.

Scheme 1

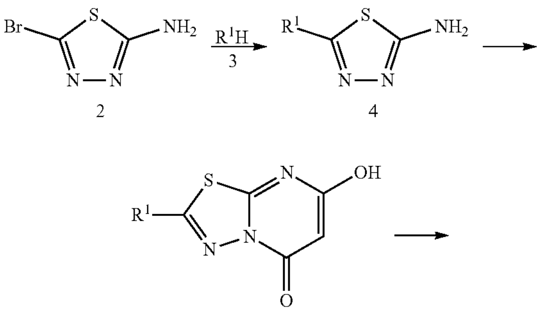

2 4 5

-continued

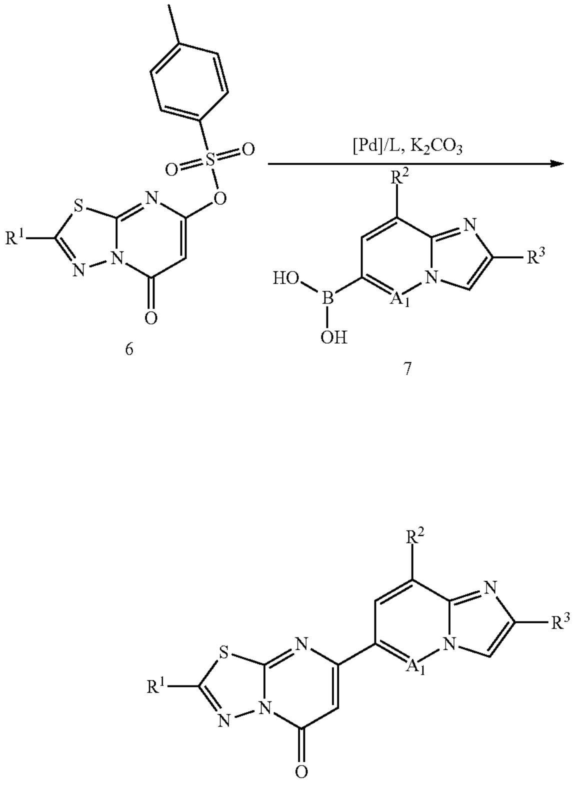

6 7

(I)

The preparation of compounds of formula (I) wherein $R^1$ is nitrogen-linked. In a first step commercially available 2-Amino-5-bromo-1,3,4-thiadiazole 2 is subject of N-arylation with eventually protected $R^1H$ 3 under SNAr conditions, to yield derivatives 4 (Scheme 1). Compounds 4 undergo a thermal cyclization with an activated malonic acid diester to deliver derivatives 5, which upon reaction with p-toluenesulfonyl chloride give rise to 6. A Suzuki cross coupling between 6 and an appropriate boronic acid 7 yield, upon eventual acid-mediated protecting group cleavage, the compound of formula (I).

Scheme 2

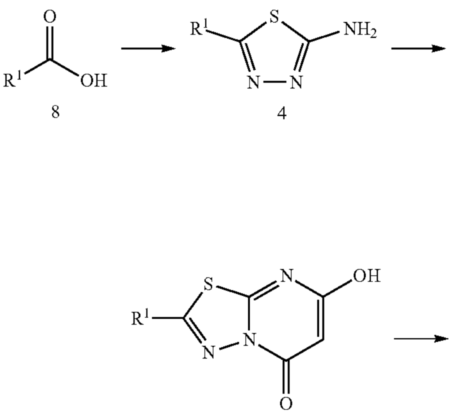

8 4 5

-continued

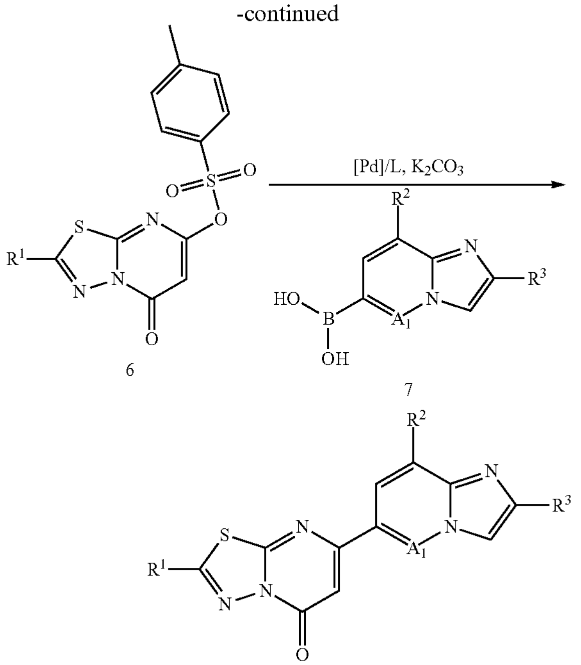

6

7

(I)

The preparation of compounds of formula (I) wherein $R^1$ is carbon-linked. Starting from suitably protected carboxylic acids-containing $R^1$ 8, formation of the corresponding acyl chloride and reaction with excess thiosemicarbazide followed by intramolecular cyclo-dehydration yield carbon-linked derivatives 4. In a similar fashion to scheme 1, thermal cyclization using an activated malonic acid diester yield compounds 5, which upon reaction with p-toluene-sulfonyl chloride give rise to 6. A Suzuki cross coupling between 6 and an appropriate boronic acid 7 yield, upon reductive or acid-mediated protecting group cleavage, the compound of formula (I).

Scheme 3

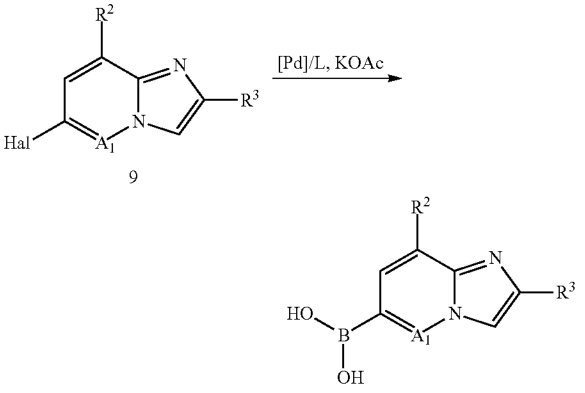

9

7

Boronic acids of formula 7 used in schemes 1 and 2 can be prepared according to scheme 3, starting from the appropriate halogen-substituted heteroaryl compound 9. The borylation reaction is carried out under Miyaura conditions in $CH_3CN$, 1,4-Dioxane or a mixture of both, as described in WO2019057740.

The invention thus also relates to a process for the preparation of a compound according to the invention, comprising at least one of the following steps (a) the reaction of compound of formula (B1)

(B1)

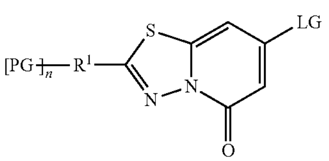

with a compound of formula (B2)

(B2)

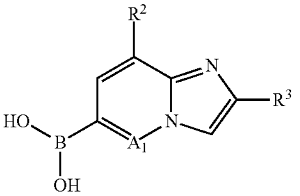

in a suitable solvent in the presence of a base and a suitable palladium catalyst, wherein n is 0 or 1, and wherein LG is a suitable leaving group, to arrive at a compound of formula (B3)

(B3)

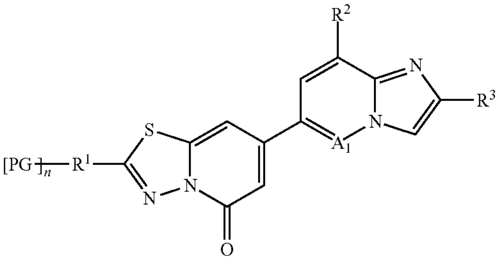

(b) the reaction of the compound of formula (B3), wherein n is 1, in a suitable solvent and in presence of TMSI to yield the compound of formula (I)

(I)

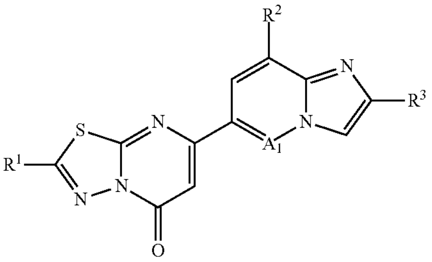

wherein in the process $R^1$, $R^2$, $R^3$, $R^4$ and $A_1$ are as defined above, and PG is a protecting group.

The reaction of step (a) can be conveniently carried out in a solvent. The solvent can be for example 1,4-dioxane, acetonitrile, water or a mixture thereof;

In the reaction of step (a), the base can be for example $K_2CO_3$, $Li_2CO_3$, $Na_2CO_3$, KOtBu, NaOtBu or LiOtBu, in particular $K_2CO_3$;

In the reaction of step (a), the palladium catalyst can be for example $Pd(dppf)Cl_2 \cdot CH_2Cl_2$ (0.2 eq. CAS #95464-05-4) or XPhos PdG4 CAS #1599466-81-5;

In the reaction of step (a), the leaving group can be for example tosylate, mesylate or halogen;

Convenient conditions for the reaction of step (a) are around 20° C.-150° C., particularly around 40° C.-130° C., more particularly around 60° C.-110° C., in particular around 90° C.;

Particular conditions for the reaction of step (a) are the use of $K_2CO_3$ in 1,4-dioxane, acetonitrile, water or a mixture thereof at around 90° C. for around 2 hrs-8 hrs;

The reaction of step (b) can be conveniently carried out in a solvent. The solvent can be for example $CH_2Cl_2$ or 1,4-dioxane;

Convenient conditions for the reaction of step (b) are around 0° C.-60° C., particularly around 50° C.-50° C., more particularly around 10° C.-40° C., in particular around 20° C.;

Particular conditions for the reaction of step (a) are the use $CH_2Cl_2$ at around 20° C. for around 1 hrs-3 hrs;

In the process, the protecting group can be for example Cbz, Boc, Fmoc or Teoc, in particular Cbz;

The invention also relates to a compound according to the invention when manufactured according to a process of the invention.

The invention thus also relates in particular to:

A compound according to the invention for use as therapeutically active substance;

A pharmaceutical composition comprising a compound according to the invention and a therapeutically inert carrier;

A compound according to the invention for use in the treatment or prophylaxis of a neurodegenerative disease;

A compound according to the invention for use in the treatment or prophylaxis of Huntington's disease;

The use of a compound according to the invention for the treatment or prophylaxis of a neurodegenerative disease, in particular Huntington's disease;

The use of a compound according to the invention for the preparation of a medicament for the treatment or prophylaxis of a neurodegenerative disease, in particular Huntington's disease; and A method for the treatment or prophylaxis of a neurodegenerative disease, in particular Huntington's disease, which method comprises administering an effective amount of a compound according to the invention to a patient in need thereof.

A certain embodiment of the invention relates to a pharmaceutical composition comprising the compound of formula (I) as described herein, or a pharmaceutically acceptable salt thereof, and a pharmaceutically acceptable auxiliary substance.

Furthermore, the invention includes all substituents in its corresponding deuterated form, wherever applicable, of the compound of formula (I).

Furthermore, the invention includes all optical isomers, i.e. diastereoisomers, diastereomeric mixtures, racemic mixtures, all their corresponding enantiomers and/or tautomers as well as their solvates, wherever applicable, of the compound of formula (I).

The compound of formula (I) may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

Also an embodiment of the present invention is a compound of formula (I) as described herein, when manufactured according to any one of the described processes.

The compound of formula (I) or a pharmaceutically acceptable salt thereof can be used as a medicament (e.g. in the form of a pharmaceutical preparation). The pharmaceutical preparation can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compound of formula (I) or a pharmaceutically acceptable salt thereof can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparation can contain preservatives, solubilizers, viscosity-increasing substances, stabilizers, wetting agents, emulsifiers, sweeteners, colorants, flavorants, salts for varying the osmotic pressure, buffers, masking agents or antioxidants. The pharmaceutical preparation can also contain still other therapeutically valuable substances.

The dosage can vary in wide limits and will be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Pharmaceutical Compositions

The compound of formula (I) or a pharmaceutically acceptable salt thereof can be used as a therapeutically active substance, e.g. in the form of a pharmaceutical preparation. The pharmaceutical preparation can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compound of formula (I) or a pharmaceutically acceptable salt thereof can be processed with pharmaceutically inert, inorganic or organic carriers for the production of a pharmaceutical preparation. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semiliquid or liquid polyols and the like.

The pharmaceutical preparation can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula (I) or a pharmaceutically acceptable salt thereof and a therapeutically inert carrier are also provided by the present invention, as is a process for their production, which comprises bringing a compound of formula (I) and/or pharmaceutically acceptable salts thereof and, if desired, one or more other therapeutically valuable substances into a galenical administration form together with one or more therapeutically inert carriers.

The dosage can vary within wide limits and will, have to be adjusted to the individual requirements in each particular case. In the case of oral administration the dosage for adults can vary from about 0.01 mg to about 1000 mg per day of a compound of general formula (I) or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparation conveniently contains about 1-500 mg, particularly 1-100 mg, of a compound of formula (I). Examples of compositions according to the invention are:

EXAMPLE A

Tablets of the following composition are manufactured in the usual manner:

TABLE 1 possible tablet composition

| ingredient | mg/tablet 5 | 25 | 100 | 500 |
|---|---|---|---|---|
| Compound of formula (I) | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 2 possible capsule ingredient composition

| ingredient | mg/capsule 5 | 25 | 100 | 500 |
|---|---|---|---|---|
| Compound of formula (I) | 5 | 25 | 100 | 500 |
| Hydrous Lactose | 159 | 123 | 148 | — |
| Corn Starch | 25 | 35 | 40 | 70 |

TABLE 2-continued

| possible capsule ingredient composition | | | | |
|---|---|---|---|---|
| | mg/capsule | | | |
| ingredient | 5 | 25 | 100 | 500 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula (I), lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3

| possible soft gelatin capsule ingredient composition | |
|---|---|
| ingredient | mg/capsule |
| Compound of formula (I) | 5 |
| Yellow wax | 8 |
| Hydrogenated Soya bean oil | 8 |
| Partially hydrogenated plant oils | 34 |
| Soya bean oil | 110 |
| Total | 165 |

TABLE 4

| possible soft gelatin capsule composition | |
|---|---|
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula (I) is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5

| possible suppository composition | |
|---|---|
| ingredient | mg/supp. |
| Compound of formula (I) | 15 |
| Suppository mass | 1285 |
| Total | 1300 |

Manufacturing Procedure

The suppository mass is melted in a glass or steel vessel, mixed thoroughly and cooled to Thereupon, the finely powdered compound of formula (I) is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 6

| possible injection solution composition | |
|---|---|
| ingredient | mg/injection solution. |
| Compound of formula (I) | 3 |
| Polyethylene Glycol 400 | 150 |
| acetic acid | q.s. ad pH 5.0 |
| water for injection solutions | ad 1.0 ml |

Manufacturing Procedure

The compound of formula (I) is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7

| possible sachet composition | |
|---|---|
| ingredient | mg/sachet |
| Compound of formula (I) | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula (I) is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

Abbreviations

ACN: acetonitrile; Boc: tert-butyloxycarbonyl; Cbz: carbobenzyloxy; DCM: dichloromethane; DMF: dimethylformamide; DMSO: dimethyl sulfoxide; dppf: bis(diphenylphosphino)ferrocene; ES: electron spray; EtOAc: ethyl acetate; HPLC: high performance liquid chromatography; HTRF: homogeneous time resolved fluorescence; MeOH: methanol; MS: mass spectrometry; MTBE: methyl tert-butyl ether; PPTS: pyridinium p-toluenesulfonate; RT: room temperature; TEA: triethylamine; TFA: trifluoroacetic acid; THF: tetrahydrofuran; TMSI: trimethylsilyl iodide.

The following examples are provided for illustration of the invention. They should not be considered as limiting the scope of the invention, but merely as being representative thereof.

Synthesis of intermediates 6: N-linked thiadiazoles

Intermediate 6-1 tert-butyl 4-[5-oxo-7-(p-tolylsulfonyloxy)-[1,3,4]thiadiazolo[3,2-a]pyrimidin-2-yl]piperazine-1-carboxylate

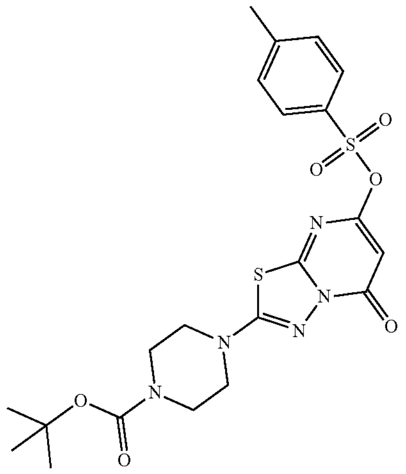 [SMILES: Cc1ccc(S(=O)(=O)Oc2cc(=O)n3nc(N4CCN(C(=O)OC(C)(C)C)CC4)sc3n2)cc1]

Step 1: In a round bottom flask, 5-bromo-1,3,4-thiadiazol-2-amine (500.0 mg, 2.78 mmol) was dissolved in DMF (5 mL) together with potassium carbonate (768 mg, 5.55 mmol) followed by 1-BOC-piperazine (621 mg, 3.33 mmol). The reaction mixture was stirred at 80° C. for 16 hours, cooled to room temperature, filtered on a frit and concentrated in vacuum. The crude material was purified by HPLC (20-70% 0-5 min $H_2O$/MeOH), flow: 30 ml/min (loading pump 4 ml/min methanol) target mass 285.37. Column: Chromatorex 18 SMB100-5T 100×19 mm 5 um) to give tert-butyl 4-(5-amino-1,3,4-thiadiazol-2-yl)piperazine-1-carboxylate (297 mg, 36% yield) as a light brown powder. MS (ES+) m/z: 286.2 [(M+H)+]

Step 2: To a suspension of tert-butyl 4-(5-amino-1,3,4-thiadiazol-2-yl)piperazine-1-carboxylate (100.0 mg, 0.350 mmol) in toluene (2 mL) malonic acid bis(2,4,6-trichlorophenyl)ester (170 mg, 0.370 mmol) was added and the mixture was heated at 90° C. for 3 h. The mixture was cooled, the precipitated was filtered, washed with toluene and MTBE and dried to afford crude tert-butyl 4-(7-hydroxy-5-oxo-[1,3,4]thiadiazolo[3,2-a]pyrimidin-2-yl)piperazine-1-carboxylate (93 mg, 71% yield) as a white powder. MS (ES+) m/z: 354.0 $[(M+H)^+]$ Step 3: To a solution of tert-butyl 4-(7-hydroxy-5-oxo-[1,3,4]thiadiazolo[3,2-a]pyrimidin-2-yl)piperazine-1-carboxylate (283.0 mg, 0.800 mmol) in THF (10 mL) triethylamine (0.22 mL, 1.6 mmol) and p-toluenesulfonyl chloride (229.0 mg, 1.2 mmol) were added sequentially and the mixture stirred for 16 hours at room temperature. The mixture was evaporated to dryness and the residue purified by HPLC (40-90% 0-5 min $H_2O$/MeOH), flow: 30 ml/min (loading pump 4 ml/min methanol) target mass 507.59. Column: YMC Triart C18 100×20 mm, 5 um) to give tert-butyl 4-[5-oxo-7-(p-tolylsulfonyloxy)-[1,3,4]thiadiazolo[3,2-a]pyrimidin-2-yl]piperazine-1-carboxylate (375 mg, 87.7% yield) as a light brown solid. MS (ES+) m/z: 508.2 $[(M+H)^+]$

Intermediate 6-2 tert-butyl (2S,6R)-2,6-dimethyl-4-[5-oxo-7-(p-tolylsulfonyloxy)-[1,3,4]thiadiazolo[3,2-a]pyrimidin-2-yl]piperazine-1-carboxylate

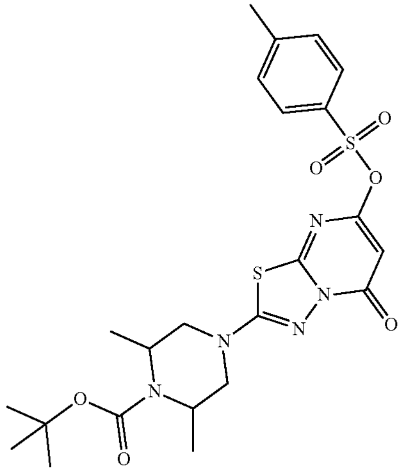 [SMILES: Cc1ccc(S(=O)(=O)Oc2cc(=O)n3nc(N4CC(C)N(C(=O)OC(C)(C)C)C(C)C4)sc3n2)cc1]

Step 1: In analogy to the preparation of intermediate 6-1 (step 1), starting from 5-bromo-1,3,4-thiadiazol-2-amine (2.0 g, 11.11 mmol) in DMF (20 mL) together with potassium carbonate (3.1 g, 22.22 mmol) followed by tert-butyl (2R,6S)-2,6-dimethylpiperazine-1-carboxylate (2.5 g, 11.66 mmol), tert-butyl (2R,6 S)-4-(5-amino-1,3,4-thiadiazol-2-yl)-2,6-dimethyl-piperazine-1-carboxylate (2.3 g, 66% yield) was obtained as a light brown solid. MS (ES+) m/z: 314.2 $[(M+H)^+]$ Step 2: In analogy to the preparation of intermediate 6-1 (step 2) From tert-butyl (2 S,6R)-4-(5-amino-1,3,4-thiadiazol-2-yl)-2,6-dimethyl-piperazine-1-carboxylate (1.0 g, 3.19 mmol) and malonic acid bis(2,4,6-trichlorophenyl)ester (1.55 g, 3.35 mmol) in toluene (20 mL), tert-butyl (2S,6R)-4-(7-hydroxy-5-oxo-[1,3,4]thiadiazolo[3,2-a]pyrimidin-2-yl)-2,6-dimethyl-piperazine-1-carboxylate (1.05 g, 84.5% yield) was obtained as a white powder. MS (ES+) m/z: 382.2 $[(M+H)^+]$ Step 3: In analogy to the preparation of intermediate 6-1 (step 3), starting from tert-butyl (2 S,6R)-4-(7-hydroxy-5-oxo-[1,3,4]thiadiazolo[3,2-a]pyrimidin-2-yl)-2,6-dimethyl-piperazine-1-carboxylate (300.0 mg, 0.790 mmol), triethylamine (0.22 mL, 1.57 mmol) and p-toluenesulfonyl chloride (225.0 mg, 1.18 mmol) in THF (10 mL), tert-butyl (2S,6R)-2,6-dimethyl-4-[5-oxo-7-(p-tolylsulfonyloxy)-[1,3,4]thiadiazolo[3,2-a]pyrimidin-2-yl]piperazine-1-carboxylate (231 mg, 55% yield) was obtained as a grey solid. MS (ES+) m/z: not detectable $[(M+H)^+]$ Intermediate 6-3

[2-[(8aS)-3,4,6,7,8,8a-hexahydro-1H-pyrrolo[1,2-a]pyrazin-2-yl]-5-oxo-[1,3,4]thiadiazolo[3,2-a]pyrimidin-7-yl]4-methylbenzenesulfonate

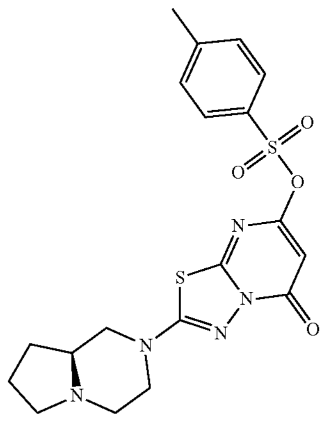 [SMILES: Cc1ccc(S(=O)(=O)Oc2cc(=O)n3nc(N4CCN5CCC[C@H]5C4)sc3n2)cc1]

Step 1: In analogy to the preparation of intermediate 6-1 (step 1), starting from 5-bromo-1,3,4-thiadiazol-2-amine (642.0 mg, 3.57 mmol) together with potassium carbonate (821.0 mg, 5.94 mmol) in DMF (5 mL), followed by (8aS)-1,2,3,4,6,7,8,8a-octahydropyrrolo[1,2-a]pyrazine (500.0 mg, 3.96 mmol), 5-[(8aS)-3,4,6,7,8,8a-hexahydro-1H-pyrrolo[1,2-a]pyrazin-2-yl]-1,3,4-thiadiazol-2-amine (385 mg, 41% yield) was obtained as a brown powder. MS (ES+) m/z: 226.2

Step 2: In analogy to the preparation of intermediate 6-1 (step 2), from 5-[(8aS)-3,4,6,7,8,8a-hexahydro-1H-pyrrolo[1,2-a]pyrazin-2-yl]-1,3,4-thiadiazol-2-amine (385.0 mg, 1.71 mmol) and malonic acid bis(2,4,6-trichlorophenyl)ester (831.0 mg, 1.79 mmol) in m-xylene (5 mL), 2-[(8a S)-3,4,6,7,8,8a-hexahydro-1H-pyrrolo[1,2-a]pyrazin-2-yl]-7-hydroxy-[1,3,4]thiadiazolo[3,2-a]pyrimidin-5-one (400 mg, 72% yield) was obtained as an orange powder. MS (ES+) m/z: 294.2 $[(M+H)^+]$ Step 3: In analogy to the preparation of intermediate 6-1 (step 3), starting from 2-[(8aS)-3,4,6,7,8,8a-hexahydro-1H-pyrrolo[1,2-a]pyrazin-2-yl]-7-hydroxy-[1,3,4]thiadiazolo[3,2-a]pyrimidin-5-one (400.0 mg, 1.36 mmol), triethylamine (0.29 mL, 2.05 mmol) and p-toluenesulfonyl chloride (286.0 mg, 1.5 mmol) in THF (10 mL), [2-[(8aS)-3,4,6,7,8,8a-hexahydro-1H-pyrrolo[1,2-a]pyrazin-2-yl]-5-oxo-[1,3,4]thiadiazolo[3,2-a]pyrimidin-7-yl]4-methylbenzenesulfonate (93 mg, 15% yield) was obtained as a light yellow solid.

MS (ES+) m/z: 448.0 $[(M+H)^+]$

Intermediate 6-4

Benzyl 7-[5-oxo-7-(p-tolylsulfonyloxy)-[1,3,4]thiadiazolo[3,2-a]pyrimidin-2-yl]-4,7-diazaspiro[2.5]octane-4-carboxylate

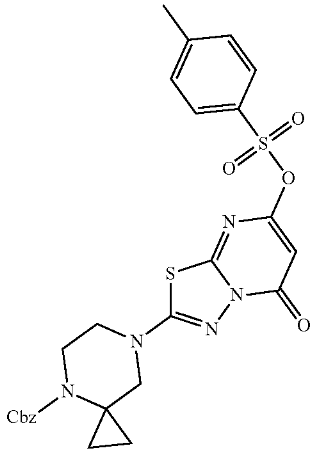 [SMILES: Cc1ccc(S(=O)(=O)Oc2cc(=O)n3nc(N4CCN(C(=O)OCc5ccccc5)C5(CC5)C4)sc3n2)cc1]

Step 1: In analogy to the preparation of intermediate 6-1 (step 1), starting from 5-bromo-1,3,4-thiadiazol-2-amine (242 mg, 1.34 mmol) together with potassium carbonate (587.0 mg, 4.24 mmol) in DMF (2 mL), followed by benzyl 4,7-diazaspiro[2.5]octane-4-carboxylate hydrochloride (400.0 mg, 1.41 mmol), benzyl 7-(5-amino-1,3,4-thiadiazol-2-yl)-4,7-diazaspiro[2.5]octane-4-carboxylate (380 mg, 74% yield) was obtained as a light brown foam. MS (ES+) m/z: 346.0

Step 2: In analogy to the preparation of intermediate 6-1 (step 2), from benzyl 7-(5-amino-1,3,4-thiadiazol-2-yl)-4,7-diazaspiro[2.5]octane-4-carboxylate (380.0 mg, 1.1 mmol) and malonic acid bis(2,4,6-trichlorophenyl)ester (535.0 mg, 1.16 mmol) in toluene (10 mL), benzyl 7-(7-hydroxy-5-oxo-[1,3,4]thiadiazolo[3,2-a]pyrimidin-2-yl)-4,7-diazaspiro[2.5]octane-4-carboxylate (315 mg, 69% yield) was obtained as a white solid. MS (ES+) m/z: 414.2 $[(M+H)^+]$ Step 3: In analogy to the preparation of intermediate 6-1 (step 3), starting from benzyl 7-(7-hydroxy-5-oxo-[1,3,4]thiadiazolo[3,2-a]pyrimidin-2-yl)-4,7-diazaspiro[2.5]octane-4-carboxylate (315.0 mg, 0.760 mmol) triethylamine (0.16 mL, 1.14 mmol) and p-toluenesulfonyl chloride (160.0 mg, 0.840 mmol) in THF (5 mL), benzyl 7-[5-oxo-7-(p-tolylsulfonyloxy)-[1,3,4]thiadiazolo[3,2-a]pyrimidin-2-yl]-4,7-diazaspiro[2.5]octane-4-carboxylate (279 mg, 63% yield) was obtained as a light brown solid. MS (ES+) m/z: 568.2 $[(M+H)^+]$ Synthesis of intermediates 6: C-linked thiadiazoles Intermediate 6-5

Benzyl 4-[5-oxo-7-(p-tolylsulfonyloxy)-[1,3,4]thiadiazolo[3,2-a]pyrimidin-2-yl]piperidine-1-carboxylate

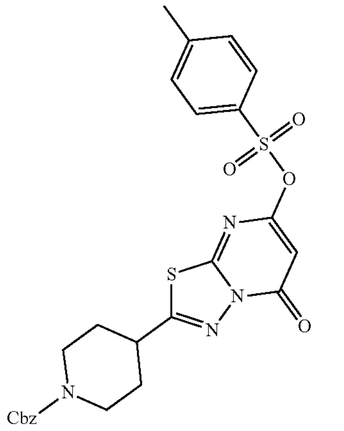 [SMILES: Cc1ccc(S(=O)(=O)Oc2cc(=O)n3nc(C4CCN(C(=O)OCc5ccccc5)CC4)sc3n2)cc1]

Step 1: In a round bottom flask, a solution of 1-[(benzyloxy)carbonyl]piperidine-4-carboxylic acid (1 g, 3.8 mmol) in $CH_2Cl_2$ (20 mL) containing a catalytic amount of DMF was treated with oxalyl chloride (0.72 g, 5.7 mmol) dropwise, and the mixture was left stirring for 1 hour at room temperature. The solvent was evaporated and the residue dissolved in THF (30 mL) and thiosemicarbazide (0.69 g, 7.6 mmol) was added portion wise. The resulting mixture was stirred at 20° C. until completion and then solvent was evaporated to dryness. The residue was suspended in phosphorus oxychloride (10.0 mL, 107.3 mmol) and stirred at 20° C. for 15 hours; alternatively, the mixture can be heated up to 65° C. until completion, usually between 2 to 4 hours. The mixture was concentrated, the residue suspended with saturated sodium carbonate solution and stirred for 1 hour. The precipitated solid was filtered on frit and dried to afford (550 mg, 44% yield) as a white powder. The product was then used in the next step without further purification. MS (ES+) m/z: 319.4 $[(M+H)^+]$ Step 2: To a suspension of benzyl 4-(5-amino-1,3,4-thiadiazol-2-yl)piperidine-1-carboxylate (550.0 mg, 1.73 mmol) in toluene (10 mL) malonic acid bis(2,4,6-trichlorophenyl)ester (880 mg, 1.9 mmol) was added and the mixture was heated at 90° C. for 3 h. The mixture was cooled, the precipitated was filtered, washed with toluene and MTBE and dried to afford crude benzyl 4-(7-hydroxy-5-oxo-8,8a-dihydro-[1,3,4]thiadiazolo[3,2-a]pyrimidin-2-yl)piperidine-1-carboxylate (500 mg, 72% yield) as a white solid. MS (ES+) m/z: 387.2 $[(M+H)^+]$ Step 3: To a solution of benzyl 4-(7-hydroxy-5-oxo-8,8a-dihydro-[1,3,4]thiadiazolo[3,2-a]pyrimidin-2-yl)piperidine-1-carboxylate (500.0 mg, 1.29 mmol) in THF (15 mL), triethylamine (0.27 mL, 1.93 mmol) and p-toluenesulfonyl chloride (319 mg, 1.67 mmol) were added sequentially and the mixture was stirred at 20° C. for 5 hours and then concentrated. The residue was dissolved in EtOAc (30 mL), washed with sat.sodium bicarbonate solution followed by water, dried over sodium sulfate and concentrated. The residue was purified by HPLC (40-65% 0-5 min $H_2O$/ACN) flow: 30 ml/min (loading pump 4 ml/min ACN) target mass 540.62 column: Chromatorex 18 SMB100-5T 100×19 mm 5 um) to afford benzyl 4-[5-oxo-7-(p-tolylsulfonyloxy)-[1,3,4]thiadiazolo[3,2-a]pyrimidin-2-yl]piperidine-1-carboxylate (329 mg, 47% yield) as a brown viscous oil. MS (ES+) m/z: 541.0 $[(M+H)^+]$ Intermediate 6-6

Benzyl 7-[5-oxo-7-(p-tolylsulfonyloxy)-[1,3,4]thiadiazolo[3,2-a]pyrimidin-2-yl]-4-azaspiro[2.5]octane-4-carboxylate

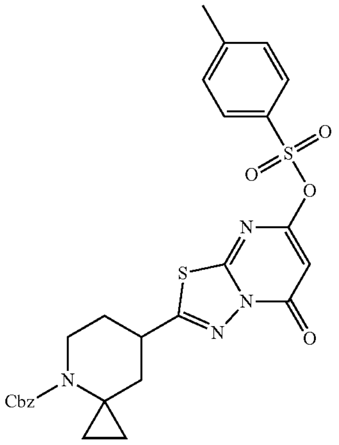 [SMILES: Cc1ccc(S(=O)(=O)Oc2cc(=O)n3nc(C4CCN(C(=O)OCc5ccccc5)C5(CC5)C4)sc3n2)cc1]

Step 1: In analogy to the preparation of intermediate 6-5 (step 1), starting from 4-benzyloxycarbonyl-4-azaspiro[2.5]octane-7-carboxylic acid (1.3 g, 4.5 mmol) in $CH_2Cl_2$ (20 mL), catalytic DMF and oxalyl chloride (0.58 mL, 6.74), followed by thiosemicarbazide (0.82 g, 9.0 mmol) in THF (30 mL) and finally by phosphorus oxychloride (11.83 mL, 126.92 mmol). Benzyl 7-(5-amino-1,3,4-thiadiazol-2-yl)-4-azaspiro[2.5]octane-4-carboxylate (1.4 g, 86% yield) was obtained as a light brown solid. MS (ES+) m/z: 345.2 $[(M+H)^+]$ Step 2: In analogy to the preparation of intermediate 6-5 (step 2). From benzyl 7-(5-amino-1,3,4-thiadiazol-2-yl)-4-azaspiro[2.5]octane-4-carboxylate (1.4 g, 4.06 mmol) and malonic acid bis(2,4,6-trichlorophenyl)ester (1.98 g, 4.27 mmol) in toluene (20 mL), benzyl 7-(7-hydroxy-5-oxo-[1,3,4]thiadiazolo[3,2-a]pyrimidin-2-yl)-4-azaspiro[2.5]octane-4-carboxylate (820 mg, 30% yield) was obtained as a yellow solid. MS (ES+) m/z: 413.2 $[(M+H)^+]$ Step 3: In analogy to the preparation of intermediate 6-5 (step 3), starting from benzyl 7-(7-hydroxy-5-oxo-[1,3,4]thiadiazolo[3,2-a]pyrimidin-2-yl)-4-azaspiro[2.5]octane-4-carboxylate (820.0 mg, 1.23 mmol), triethylamine (0.34 mL, 2.47 mmol) and p-toluenesulfonyl chloride (352.49 mg, 1.85 mmol) in THF (10 mL), 7-[5-oxo-7-(p-tolylsulfonyloxy)-[1,3,4]thiadiazolo[3,2-a]pyrimidin-2-yl]-4-azaspiro[2.5]octane-4-carboxylate (123 mg, 16.73% yield) was obtained as a yellow gum. MS (ES+) m/z: 567.2 $[(M+H)^+]$ Intermediate 6-7

Benzyl 4-fluoro-4-[5-oxo-7-(p-tolylsulfonyloxy)-[1,3,4]thiadiazolo[3,2-a]pyrimidin-2-yl]piperidine-1-carboxylate

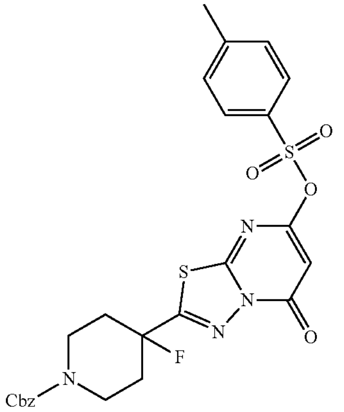 [SMILES: Cc1ccc(S(=O)(=O)Oc2cc(=O)n3nc(C4(F)CCN(C(=O)OCc5ccccc5)CC4)sc3n2)cc1]

Step 1: In analogy to the preparation of intermediate 6-5 (step 1), starting from 1-benzyloxycarbonyl-4-fluoro-piperidine-4-carboxylic acid (1.2 g, 4.3 mmol) in $CH_2Cl_2$ (15 mL), catalytic DMF and oxalyl chloride (0.55 mL, 6.4 mmol), followed by thiosemicarbazide (0.78 g, 8.5 mmol) in THF (30 mL) and finally by phosphorus oxychloride (3.98 mL, 42.66 mmol). Benzyl 4-(5-amino-1,3,4-thiadiazol-2-yl)-4-fluoro-piperidine-1-carboxylate (145 mg, 9% yield) was obtained as a white powder. MS (ES+) m/z: 337.2 [$(M+H)^+$]

Step 2: In analogy to the preparation of intermediate 6-5 (step 2). From benzyl 4-(5-amino-1,3,4-thiadiazol-2-yl)-4-fluoro-piperidine-1-carboxylate (145.0 mg, 0.43 mmol) and malonic acid bis(2,4,6-trichlorophenyl)ester (209.5 mg, 0.45 mmol) in toluene (5 mL), benzyl 4-fluoro-4-(7-hydroxy-5-oxo-[1,3,4]thiadiazolo[3,2-a]pyrimidin-2-yl)piperidine-1-carboxylate (120 mg, 34% yield) was obtained as a light yellow solid. MS (ES+) m/z: 405.2 [$(M+H)^+$]

Step 3: In analogy to the preparation of intermediate 6-5 (step 3), starting from benzyl 4-fluoro-4-(7-hydroxy-5-oxo-[1,3,4]thiadiazolo[3,2-a]pyrimidin-2-yl)piperidine-1-carboxylate (120.0 mg, 0.300 mmol), triethylamine (0.06 mL, 0.450 mmol) and p-toluenesulfonyl chloride (56.5 mg, 0.300 mmol) in DCM (3 mL), benzyl 4-fluoro-4-[5-oxo-7-(p-tolylsulfonyloxy)-[1,3,4]thiadiazolo[3,2-a]pyrimidin-2-yl]piperidine-1-carboxylate (34 mg, 20% yield) was obtained as a white solid. MS (ES+) m/z: 559.0 [$(M+H)^+$]

Intermediate 6-8

Benzyl 3-[5-oxo-7-(p-tolylsulfonyloxy)-[1,3,4]thiadiazolo[3,2-a]pyrimidin-2-yl]pyrrolidine-1-carboxylate

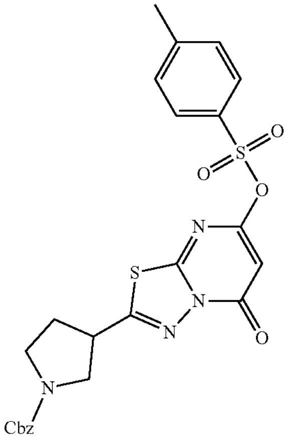 [SMILES: Cc1ccc(S(=O)(=O)Oc2cc(=O)n3nc(C4CCN(C(=O)OCc5ccccc5)C4)sc3n2)cc1]

Step 1: In analogy to the preparation of intermediate 6-5 (step 1), starting from 1-benzyloxycarbonylpyrrolidine-3-carboxylic acid (1.5 g, 6.0 mmol) in $CH_2Cl_2$ (15 mL), catalytic DMF and oxalyl chloride (0.77 mL, 9.0 mmol), followed by thiosemicarbazide (1.1 g, 12.0 mmol) in THF (30 mL) and finally by phosphorus oxychloride (5.61 mL, 60.2 mmol). Benzyl 3-(5-amino-1,3,4-thiadiazol-2-yl)pyrrolidine-1-carboxylate (1.19 g, 58.5% yield) was obtained as a yellow solid. MS (ES+) m/z: 305.2 [$(M+H)^+$]

Step 2: In analogy to the preparation of intermediate 6-5 (step 2). From benzyl 3-(5-amino-1,3,4-thiadiazol-2-yl)pyrrolidine-1-carboxylate (1.20 g, 3.52 mmol) and malonic acid bis(2,4,6-trichlorophenyl)ester (1.71 g, 3.69 mmol) in toluene (20 mL), benzyl 3-(7-hydroxy-5-oxo-[1,3,4]thiadiazolo[3,2-a]pyrimidin-2-yl)pyrrolidine-1-carboxylate (1 g, 59% yield) was obtained as a yellow solid. MS (ES+) m/z: 373.2 [$(M+H)^+$]

Step 3: In analogy to the preparation of intermediate 6-5 (step 3), starting from benzyl 3-(7-hydroxy-5-oxo-[1,3,4]thiadiazolo[3,2-a]pyrimidin-2-yl)pyrrolidine-1-carboxylate (1.0 g, 2.07 mmol), triethylamine (0.58 mL, 4.14 mmol) and p-toluenesulfonyl chloride (0.59 g, 3.1 mmol) in THF (25 mL), benzyl 3-[5-oxo-7-(p-tolylsulfonyloxy)-[1,3,4]thiadiazolo[3,2-a]pyrimidin-2-yl]pyrrolidine-1-carboxylate (396 mg, 34.5% yield) was obtained as a dark brown solid.

MS (ES+) m/z: 527.2 [$(M+H)^+$]

Synthesis of Intermediates 7: boronic acids

Intermediate 7-1

2,8-dimethyl-6-(4,4,5,5-tetramethyl-1,3,2-dioxaborolan-2-yl)imidazo[1,2-b]pyridazine

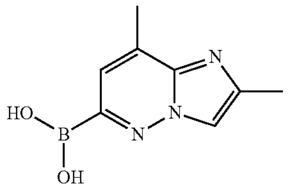

In an Argon-flushed two-neck round bottom flask, 6-chloro-2,8-dimethyl-imidazo[1,2-b]pyridazine (542.0 mg, 2.98 mmol), anhydrous potassium acetate (585 mg, 5.97 mmol) and bis(pinacolato)diboron (833.0 mg, 3.28 mmol) were suspended in anhydrous 1,4-Dioxane (25 mL) and sparged with Argon for 10 minutes. 1,1'-bis(diphenylphosphino)ferrocene-palladium(II)dichloride dichloromethane complex (244.0 mg, 0.300 mmol) was then added and the mixture heated to 95° C. until completion, usually between 2 to 6 hours. The mixture was then cooled to room temperature, diluted with THF (30 mL) and filtered over a pad of Celite pre conditioned with THF. The filtrate is evaporated to dryness and redissolved in HPLC-grade $CH_3CN$ to a concentration of 0.33 M, according to initial material input. The solution was used as such without further purification and is stable when stored at −20° C. MS (ES+) m/z: 182.0 $[(M+H)^+]$ Intermediate 7-2

8-fluoro-2-methyl-6-(4,4,5,5-tetramethyl-1,3,2-dioxaborolan-2-yl)imidazo[1,2-a]pyridine

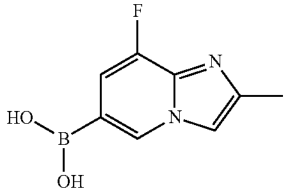

In analogy to the preparation of intermediate 7-1, starting from 6-bromo-8-fluoro-2-methyl-imidazo[1,2-a]pyridine (500.0 mg, 2.18 mmol) in 1,4-Dioxane (5 mL), potassium acetate (642 mg, 6.55 mmol), bis(pinacolato)diboron (1.39 g, 5.46 mmol) and 1, 1'-bis(diphenylphosphino)ferrocene-palladium(II)dichloride dichloromethane complex (89 mg, 0.110 mmol), to afford 8-fluoro-2-methyl-6-(4,4,5,5-tetramethyl-1,3,2-dioxaborolan-2-yl)imidazo[1,2-a]pyridine (265 mg, 31% yield) as a white solid.

Intermediate 7-3

8-fluoro-2-methyl-6-(4,4,5,5-tetramethyl-1,3,2-dioxaborolan-2-yl)imidazo[1,2-a]pyridine

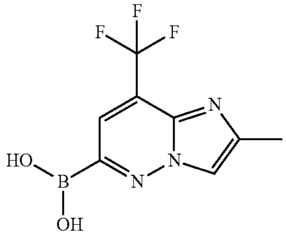 [SMILES: Cc1cn2nc(B(O)O)cc(C(F)(F)F)c2n1]

Step 1: As described in WO2015048245: 3,6-dichloro-4-(trifluoromethyl)pyridazine (9.95 g, 45.86 mmol) was dissolved in 1,4-dioxane (99.5 mL) and the solution was split into ten 20 mL Biotage microwave. Ammonia, 25% in Water (31.24 g, 39.69 mL), was added and the vials were sealed and heated at 50° C. for 15 hr. Combined reaction mixture was poured in water and extracted with EtOAc. The organic layers were washed with brine, dried over $Na_2SO_4$, filtered and evaporated in vacuo.

The residue was purified by flash chromatography eluting with EtOAc/hexanes 0-50% to obtain [6-chloro-4-(trifluoromethyl)pyridazin-3-yl]amine (2.5 g, 27.32%) as white solid. MS (ES+) m/z: 198.0 $[(M+H)^+]$ Step 2: [6-chloro-4-(trifluoromethyl)pyridazin-3-yl] amine (5.75 g, 29.11 mmol) and PPTS (731.45 mg, 2.91 mmol) were combined in isopropanol (50 mL) to give a clear solution which was treated with 1-bromo-2,2-dimethoxy-propane (6.39 g, 4.74 mL, 34.93 mmol), the resulting light yellow solution was heated to 75° C. and stirred for 20 hr. The mixture was allowed to cool to RT, diluted with EtOAc and aqueous $NaHCO_3$ and extracted. Organic layers were washed with brine, dried over $Na_2SO_4$, filtered and dried in vacuo.

The residue was purified by flash chromatography eluting with EtOAc/hexanes 0-40% to obtain 6-chloro-2-methyl-8-(trifluoromethyl)imidazo[1,2-b]pyridazine (3.8 g, 52%) as yellow solid. MS (ES+) m/z: 236.0 $[(M+H)^+]$ Step 3: In analogy to the preparation of intermediate 7-1, starting from 6-chloro-2-methyl-8-(trifluoromethyl)imidazo[1,2-b]pyridazine (720 mg, 3.06 mmol) in 1,4-Dioxane (28.8 mL), potassium acetate (900 mg, 9.18 mmol), bis(pinacolato)diboron (970 mg, 3.72 mmol) and Palladium tetrakis (177 mg, 0.153 mmol), to afford [2-methyl-8-(trifluoromethyl)imidazo[1,2-b]pyridazin-6-yl]boronic acid. MS (ES+) m/z: 246.1 $[(M+H)^+]$ General Procedure for Suzuki Cross Coupling Reaction To a solution of an intermediate 6 in 1,4-dioxane, was added 1.5 equivalent of an intermediate 7 as a 0.33 M solution in $CH_3CN$ and 4.0 equivalent of $K_2CO_3$ delivered as a 2 M aqueous solution. The reaction mixture was degassed with Argon for 5 minutes before being treated with a palladium catalyst [either $Pd(dppf)Cl_2 \cdot CH_2Cl_2$ (0.2 eq. CAS #95464-05-4) or XPhos PdG4 CAS #1599466-81-5]. The reaction mixture was heated at 90° C. until completion (usually between 2 and 8 hours), cooled to room temperature, filtered over a pad of Celite preconditioned with $CH_3CN$, washed with $CH_3CN$ and concentrated in vacuo. A purification was performed either by column chromatography or reverse phase preparative HPLC to afford the desired product.

General Procedure for Cbz Removal

To a solution of any of the abovementioned Suzuki products (containing a carbon linked $R^1$) in anhydrous $CH_2Cl_2$ cooled to 0° C., were added 4.0 equivalent of TMSI as a 1 M solution in $CH_2Cl_2$. The reaction mixture was stirred at room temperature until completion, usually between 1 and 3 hours. The mixture was then evaporated in vacuo and purified via reverse phase preparative HPLC, using a ACN/Water+0.1% TEA gradient on a Gemini NX, 12 nm, 5 μm, 100x30 mm column.

EXAMPLE 1

7-(2,8-dimethylimidazo[1,2-b]pyridazin-6-yl)-2-piperazino-[1,3,4]thiadiazolo[3,2-a]pyrimidin-5-one

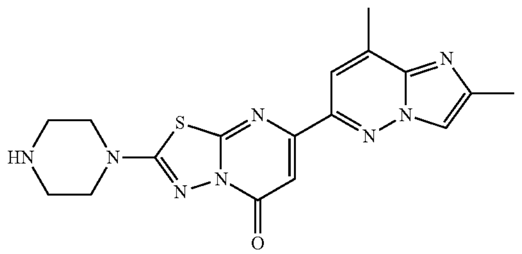 [SMILES: Cc1cn2nc(-c3cc(=O)n4nc(C5CCNCC5)sc4n3)cc(C)c2n1]

Step 1: 4-[7-(2,8-dimethylimidazo[1,2-b]pyridazin-6-yl)-5-keto-[1,3,4]thiadiazolo[3,2-a]pyrimidin-2-yl]piperazine-1-carboxylic acid tert-butyl ester

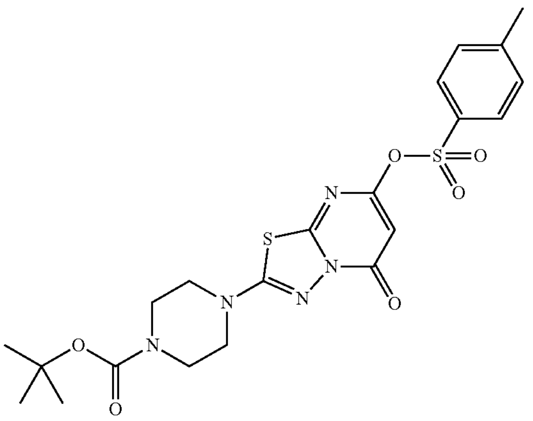

Intermediate 6-1

+

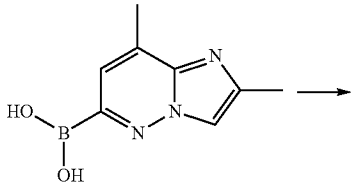

Intermediate 7-1

-continued

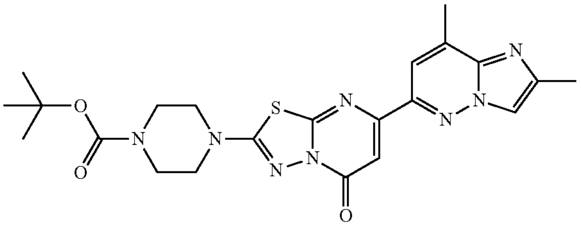

To a solution of 4-(5-keto-7-tosyloxy-[1,3,4]thiadiazolo[3,2-a]pyrimidin-2-yl)piperazine-1-carboxylic acid tert-butyl ester (intermediate 6-1) (250 mg, 0.49 mmol) in 1,4-Dioxane (2.5 mL), was added a 0.33 M solution in CH 3 CN of (2,8-dimethylimidazo[1,2-b]pyridazin-6-yl)boronic acid (2.25 mL, 0.74 mmol), intermediate 7-1, and a 2 M solution of $K_2CO_3$ (aqueous) (985 μL, 2.0 mmol). The resulting mixture was sparged with Argon for 5 minutes, treated with palladium catalyst $Pd(dppf)Cl_2 \cdot CH_2Cl_2$ (80.4 mg, 0.1 mmol), and then stirred at ° C. for 1 hour. The mixture was then cooled to room temperature, diluted with $CH_3CN$ (15 mL) and filtered on a Celite pad. Solvents were evaporated in vacuo and a column chromatography ($SiO_2$, $CH_2Cl_2$/MeOH) afforded 170 mg (55%) of 4-[7-(2,8-dimethylimidazo[1,2-b]pyridazin-6-yl)-5-keto-[1,3,4]thiadiazolo[3,2-a]pyrimidin-2-yl]piperazine-1-carboxylic acid tert-butyl ester. MS (ES+) m/z: 483.3 [$(M+H)^+$].

Step 2: 7-(2,8-dimethylimidazo[1,2-b]pyridazin-6-yl)-2-piperazino-[1,3,4]thiadiazolo[3,2-a]pyrimidin-5-one

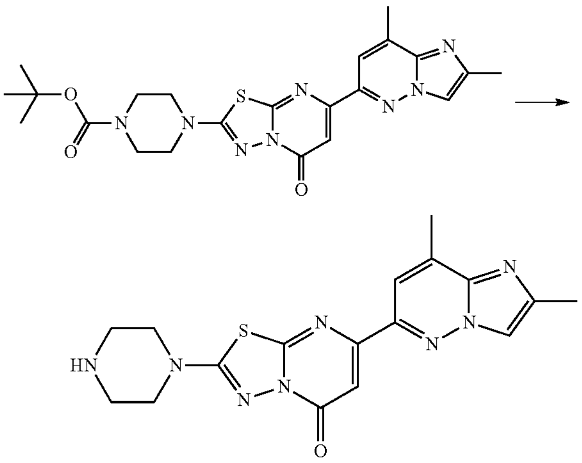

To a solution of 4-[7-(2,8-dimethylimidazo[1,2-b]pyridazin-6-yl)-5-keto-[1,3,4]thiadiazolo[3,2-a]pyrimidin-2-yl]piperazine-1-carboxylic acid tert-butyl ester (170 mg, mmol) in $CH_2Cl_2$ (2 mL) was added TFA (2 mL) and the reaction mixture was stirred at room temperature until completion, usually between 1 and 3 hours. The mixture was then evaporated in vacuo and purified via reverse phase preparative HPLC, using a ACN/Water+0.1% TEA gradient on a Gemini NX, 12 nm, 5 μm, 100x30 mm column. To afford 30 mg (29%) of 7-(2,8-dimethylimidazo[1,2-b]pyridazin-6-yl)-2-piperazino-[1,3,4]thiadiazolo[3,2-a]pyrimidin-5-one as alight yellow solid. MS (ES+) m/z: 382.1 [$(M+H)^+$].

EXAMPLE 2

7-(2,8-dimethylimidazo[1,2-b]pyridazin-6-yl)-2-(4-piperidyl)-[1,3,4]thiadiazolo[3,2-a]pyrimidin-5-one

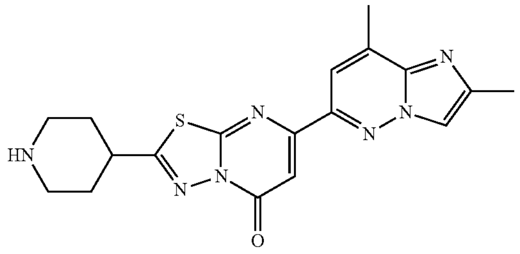

Following preparation described in example 1, using intermediates 6-5 and 7-1, afforded 24.4 mg of the title compound as a yellow solid. MS (ES+) m/z: 380.0 [(M+H)$^+$].

EXAMPLE 3

7-(8-fluoro-2-methyl-imidazo[1,2-a]pyridin-6-yl)-2-(4-piperidyl)-[1,3,4]thiadiazolo[3,2-a]pyrimidin-5-one

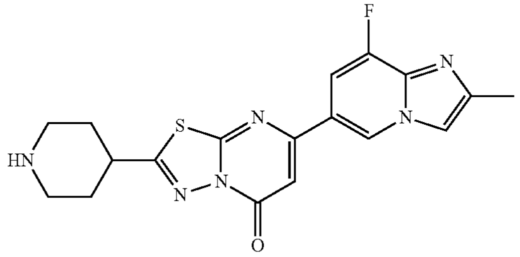 [SMILES: Cc1cn2cc(-c3cc(=O)n4nc(C5CCNCC5)sc4n3)cc(F)c2n1]

Following preparation described in example 1, using intermediates 6-5 and 7-2, afforded 11.3 mg of the title compound as a white solid. MS (ES+) m/z: 383.0 [(M+H)$^+$].

EXAMPLE 4

7-(2,8-dimethylimidazo[1,2-b]pyridazin-6-yl)-2-[(3R,5S)-3,5-dimethylpiperazin-1-yl]-[1,3,4]thiadiazolo[3,2-a]pyrimidin-5-one

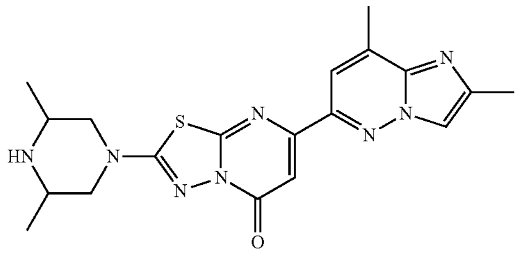 [SMILES: Cc1cn2nc(-c3cc(=O)n4nc(N5CC(C)NC(C)C5)sc4n3)cc(C)c2n1]

Following preparation described in example 1, using intermediates 6-2 and 7-1, afforded 21.8 mg of the title compound as a yellow solid. MS (ES+) m/z: 411.2 [(M+H)$^+$].

EXAMPLE 5

2-[(8aS)-3,4,6,7,8,8a-hexahydro-1H-pyrrolo[1,2-a]pyrazin-2-yl]-7-(2,8-dimethylimidazo[1,2-b]pyridazin-6-yl)-[1,3,4]thiadiazolo[3,2-a]pyrimidin-5-one

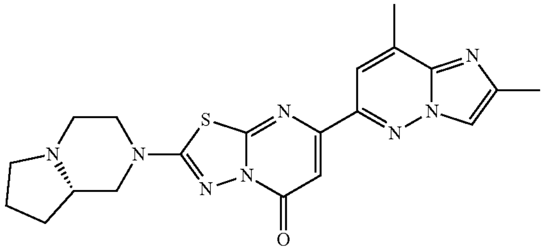 [SMILES: Cc1cn2nc(-c3cc(=O)n4nc(N5CCN6CCC[C@H]6C5)sc4n3)cc(C)c2n1]

Following preparation described in example 1, using intermediates 6-3 and 7-1, afforded 17.7 mg of the title compound as a yellow solid. MS (ES+) m/z: 423.2 [(M+H)$^+$].

EXAMPLE 6

2-(4,7-diazaspiro[2.5]octan-7-yl)-7-(2,8-dimethyl-imidazo[1,2-b]pyridazin-6-yl)-[1,3,4]thiadiazolo[3,2-a]pyrimidin-5-one

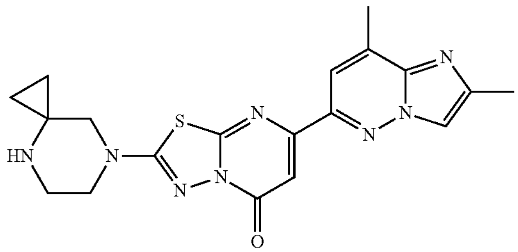

Following preparation described in example 1, using intermediates 6-4 and 7-1, afforded 39.3 mg of the title compound as a yellow solid. MS (ES+) m/z: 409.0 [(M+H)$^+$].

EXAMPLE 7

2-(4-azaspiro[2.5]octan-7-yl)-7-(2,8-dimethylimidazo[1,2-b]pyridazin-6-yl)-[1,3,4]thiadiazolo[3,2-a]pyrimidin-5-one

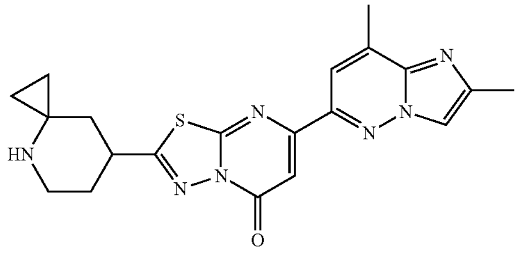

Following preparation described in example 1, using intermediates 6-6 and 7-1, afforded 13.8 mg of the title compound as a yellow solid. MS (ES+) m/z: 409.2 [(M+H)$^+$].

EXAMPLE 8

7-(2,8-dimethylimidazo[1,2-b]pyridazin-6-yl)-2-(4-fluoro-4-piperidyl)-[1,3,4]thiadiazolo[3,2-a]pyrimidin-5-one

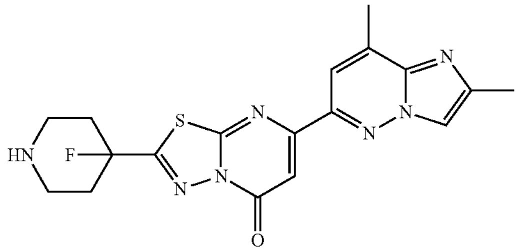

Following preparation described in example 1, using intermediates 6-7 and 7-1, afforded 8.5 mg of the title compound as a yellow solid. MS (ES+) m/z: 400.2 [(M+H)$^+$].

EXAMPLE 9

7-[2-methyl-8-(trifluoromethyl)imidazo[1,2-b]pyridazin-6-yl]-2-(4-piperidyl)-[1,3,4]thiadiazolo[3,2-a]pyrimidin-5-one

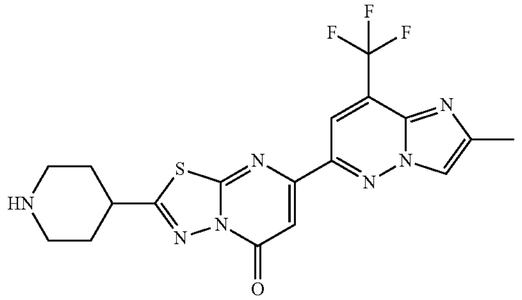

Following preparation described in example 1, using intermediates 6-5 and 7-3, afforded 30 mg of the title compound as a light yellow solid. MS (ES+) m/z: 436.1 [(M+H)$^+$].

EXAMPLE 10

7-(2,8-dimethylimidazo[1,2-b]pyridazin-6-yl)-2-pyrrolidin-3-yl-[1,3,4]thiadiazolo[3,2-a]pyrimidin-5-one

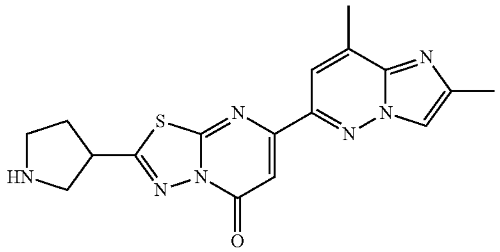

Following preparation described in example 1, using intermediates 6-8 and 7-1, afforded 20.1 mg of the title compound as a yellow solid. MS (ES+) m/z: 368.0 [(M+H)$^+$].

EXAMPLE 11

Homogeneous Time Resolved Fluorescence for HTT Lowering

The HTRF assay was adapted from Weiss et al. (Analytical Biochemistry Volume 395, Issue 1, 1 Dec. 2009, Pages 8-15 and Analytical Biochemistry Volume 410, 2011, Pages 304-306) to cells from GENEAe020-A cell line (https://hpscreg.eu/cell-line/GENEAe020-A).

Compounds were tested for the effect of mutant HTT levels in Huntington patient human cells (GENEAe020-A cell line) using Homogeneous Time Resolved Fluorescence (HTRF) directed towards mutant HTT protein (mHTT). The GENEAe020-A cell line was derived by Genea Biocells from human blastocysts of HD donors. After assessing viability, cells were plated into 384 well collagen coated plates in growth media. Once cells adhered, media was removed and test compounds dissolved in DMSO were diluted with buffer solution and added to the adherent cells. Controls included experiments with no cells, DMSO with no compound, and Hsp90 inhibitor control. Cells were incubated with compounds and controls for 48 hours. Then, the cells were lysed and transferred to an assay plate containing HTRF labeled monoclonal antibodies developed by Paul Patterson (Ko et al., Brain Research Bulletin, Volume 56, Numbers 3 and 4, 2001, Pages 319-329) which recognize specific areas of the HTT protein. The terbium labeled "donor" antibody (2B7) binds to the N-terminus of the HTT protein and the Alexa488 labeled "acceptor" antibody (MW1) is specific for the polyglutamine region of the protein. Binding of the acceptor labeled antibody is more efficient for the extended polyglutamine repeats of mutant HTT protein which translates into a signal boost which enables the specific measurement of mutant HTT protein level. The HTRF donor and acceptor detection reagents were incubated with the cell lysate and the ratio between the signals of the two fluorophores is indicative of the relative quantities of mHTT.

The results of this assay are provided in Table 1. Table 1 provides the $EC_{50}$ (half maximal effective concentration) values for the reduction of mHTT obtained for particular examples of the present invention as measured by HTRF assay (data shown below is mean from three replicates).

| Example | HTRF mHTT $EC_{50}$ (μM) |
|---|---|
| 1 | 0.821 |
| 2 | 0.196 |
| 3 | 7.395 |
| 4 | 2.042 |
| 6 | 5.840 |
| 7 | 0.302 |
| 8 | 0.315 |
| 9 | 0.700 |
| 10 | 5.22 |

The invention claimed is:

1. A compound of formula (I)

(I)

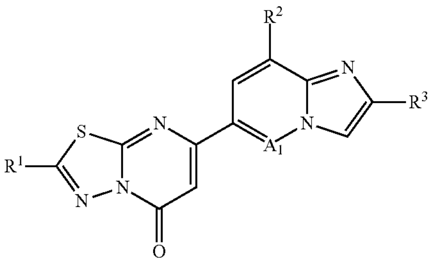

wherein:

$A_1$ is —CH— or —N—;

$R^1$ is selected from hydrogen, $C_{1-8}$ alkyl, $C_{3-10}$ cycloalkyl, $C_{6-10}$ aryl, 5-12 membered heteroaryl, and 3-12 membered heterocycloalkyl, wherein each of said $C_{3-10}$ cycloalkyl, $C_{6-10}$ aryl, 5-12 membered heteroaryl, and 3-12 membered heterocycloalkyl is optionally substituted with one, two, three or four substituents independently selected from R4;

$R^2$ is selected from hydrogen, halogen, cyano, amino, hydroxyl, $C_{1-8}$ alkyl, $C_{2-8}$ alkenyl, $C_{1-8}$ haloalkyl, $C_{1-8}$ alkoxy, $C_{1-8}$ haloalkoxy, and $C_{3-10}$ cycloalkyl;

$R^3$ is selected from hydrogen, halogen, $C_{1-8}$ alkyl, $C_{1-8}$ haloalkyl, and $C_{1-8}$ alkoxy; and $R^4$ is selected from halogen, $C_{1-8}$ alkyl, -12 membered heterocycloalkyl, 3-12 membered heterocycloalkyl-$C_{1-8}$ alkyl, $C_{1-8}$ alkyl-3-12 membered heterocycloalkyl, 3-12 membered haloheterocycloalkyl, $C_{3-10}$ cycloalkyl, $C_{3-10}$ cycloalkyl-$C_{1-8}$ alkyl, $C_{1-8}$ alkyl-$C_{3-10}$ cycloalkyl, $C_{3-10}$ halocycloalkyl, $C_{3-10}$ cycloalkyl-amino, $C_{6-10}$ aryl, $C_{6-10}$ aryl-$C_{1-8}$ alkyl, $C_{1-8}$ alkyl-$C_{6-10}$ aryl, $C_{6-10}$ haloaryl, cyano, hydroxy, oxo, $C_{1-8}$ haloalkyl, $C_{1-8}$ alkyl-carbonyl, $C_{1-8}$ alkoxy, $C_{1-8}$ haloalkoxy, $C_{1-8}$ alkoxy-$C_{1-8}$ alkyl, amino, $C_{1-8}$ alkylamino, di($C_{1-8}$ alkyl)amino, $C_{1-8}$ aminoalkyl, $C_{1-8}$ alkylamino-$C_{1-8}$ alkyl, di($C_{1-8}$ alkyl)amino-$C_{1-8}$ alkyl, $C_{1-8}$ aminoalkyl-amino, $C_{1-8}$ alkoxy-$C_{1-8}$ alkylamino, $C_{1-8}$ alkyl-carbonyl-amino, $C_{1-8}$ alkoxy-carbonyl-amino, $C_{1-8}$ hydroxy-alkyl, $C_{1-8}$ hydroxyalkoxy-$C_{1-8}$ alkyl, and $C_{1-8}$ hydroxyalkyl-amino;

or a pharmaceutically acceptable salt thereof;

provided that

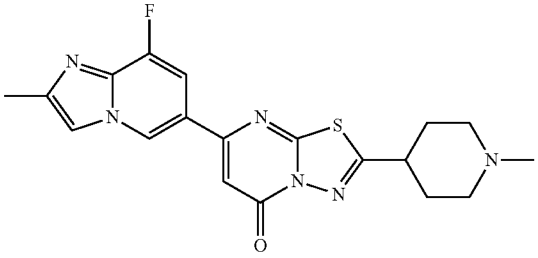

7-(8-fluoro-2-methyl-imidazo[1,2-a]pyridin-6-yl)-2-(1-methyl-4-piperidyl)-[1,3,4]thiadiazolo[3,2-a]pyrimidin-5-one

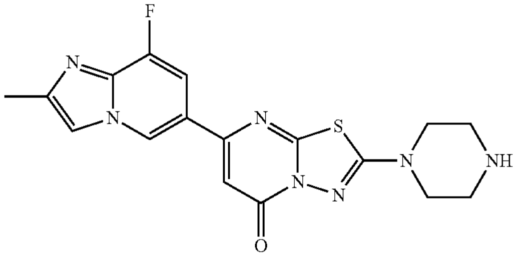

7-(8-fluoro-2-methyl-imidazo[1,2-a]pyridin-6-yl)-2-(4-piperidyl)-[1,3,4]thiadiazolo[3,2-a]pyrimidin-5-one

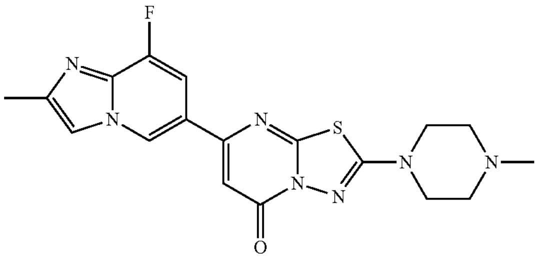

7-(8-fluoro-2-methyl-imidazo[1,2-a]pyridin-6-yl)-2-(4-methylpiperazin-1-yl)-[1,3,4]thiadiazolo[3,2-a]pyrimidin-5-one

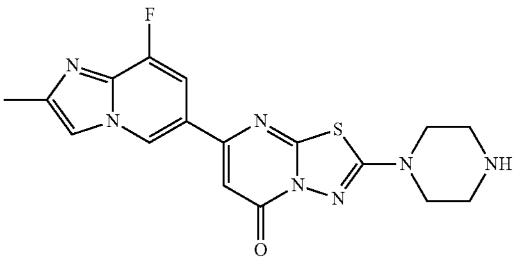

7-(8-fluoro-2-methyl-imidazo[1,2-a]pyridin-6-yl)-2-piperazin-1-yl-[1,3,4]thiadiazolo[3,2-a]pyrimidin-5-one

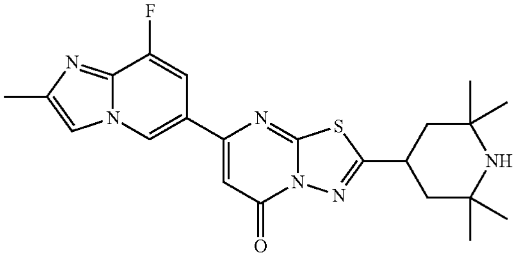

7-(8-fluoro-2-methyl-imidazo[1,2-a]pyridin-6-yl)-2-(2,2,6,6-tetramethyl-4-piperidyl)-[1,3,4]thiadiazolo[3,2-a]pyrimidin-5-one

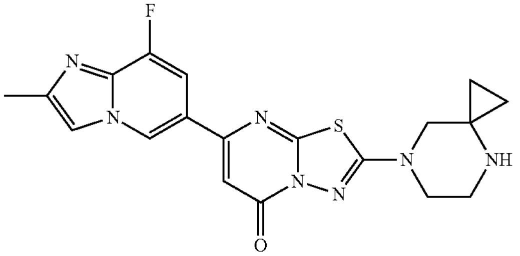

2-(4,7-diazaspiro[2.5]octan-7-yl)-7-yl(8-fluoro-2-methyl-imidazo[1,2-a]pyridin-6-yl)-[1,3,4]thiadiazolo[3,2-a]pyrimidin-5-one are excluded.

2. The compound according to claim 1, wherein $R^1$ is 3-12 membered heterocycloalkyl, optionally substituted with one or two substituents independently selected from $R^4$.

3. The compound according to claim 2, wherein $R^1$ is selected from 2-piperazinyl, 4-piperidyl, pyrrolidin-3-yl, (8aS)-3,4,6,7,8,8a-hexahydro-1H-pyrrolo[1,2-a]pyrazin-2-yl, 4,7-diazaspiro[2.5]octan-7-yl, and 4-azaspiro[2.5]octan-7-yl, each of which is optionally substituted with one or two substituents independently selected from $R^4$.

4. The compound according to claim 3, wherein $R^1$ is 4-piperidyl or 4-azaspiro[2.5]octan-7-yl, each of which is optionally substituted with one or two substituents independently selected from $R^4$.

5. The compound according to claim 1, wherein $R^2$ is selected from halogen, $C_{1-8}$ alkyl, and $C_{1-8}$ haloalkyl.

6. The compound according to claim 5, wherein $R^2$ is selected from fluoro, methyl, and trifluoromethyl.

7. The compound according to claim 1, wherein $R^3$ is $C_{1-8}$ alkyl.

8. The compound according to claim 7, wherein $R^3$ is methyl.

9. The compound according to claim 1, wherein $R^4$ is selected from halogen and $C_{1-8}$ alkyl.

10. The compound according to claim 9, wherein $R^4$ is selected from fluoro and methyl.

11. The compound according to claim 1, wherein $A_1$ is —N—.

12. The compound according to claim 1, selected from:

1

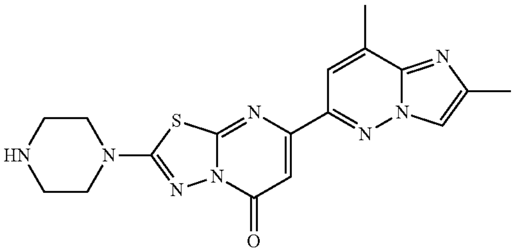

7-(2,8-dimethylimidazo[1,2-b]pyridazin-6-yl)-2-piperazino-[1,3,4]thiadiazolo[3,2-a]pyrimidin-5-one

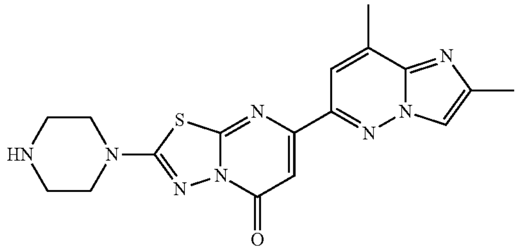

7-(2,8-dimethylimidazo[1,2-b]pyridazin-6-yl)-2-(4-piperidyl)-[1,3,4]thiadiazolo[3,2-a]pyrimidin-5-one

4

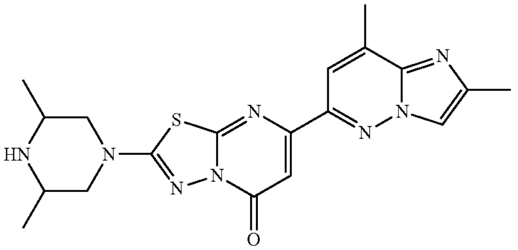

7-(2,8-dimethylimidazo[1,2-b]pyridazin-6-yl)-2-[(3R,5S)-3,5-dimethylpiperazin-1-yl]-[1,3,4]thiadiazolo[3,2-a]pyrimidin-5-one

5

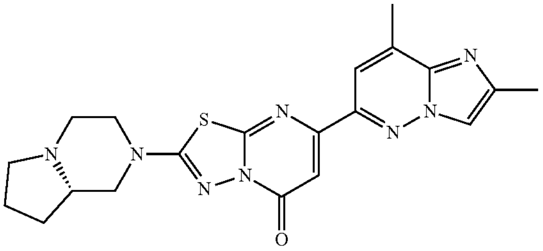

2-[(8aS)-3,4,6,7,8,8a-hexahydro-1H-pyrrolo[1,2-a]pyrazin-2-yl)-7-(2,8-dimethylimidazo[1,2-b]pyridazin-6-yl]-[1,3,4]thiadiazolo[3,2-a]pyrimidin-5-one

6

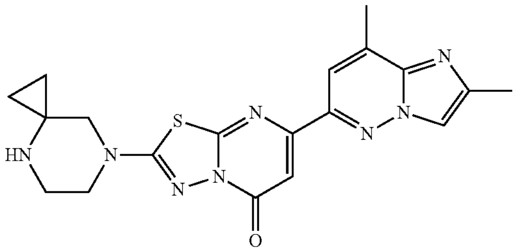

2-(4,7-diazaspiro[2.5]octan-7-yl)-7-(2,8-dimethylimidazo[1,2-b]pyridazin-6-yl)-[1,3,4]thiadiazolo[3,2-a]pyrimidin-5-one

7

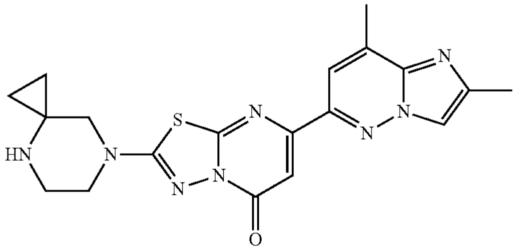 [SMILES: Cc1cn2nc(-c3cc(=O)n4nc(N5CCNC6(CC6)C5)sc4n3)cc(C)c2n1]

2-(4-azaspiro[2.5]octan-7-yl)-7-(2,8-dimethylimidazo[1,2-b]pyridazin-6-yl)-[1,3,4]thiadiazolo[3,2-a]pyrimidin-5-one

8

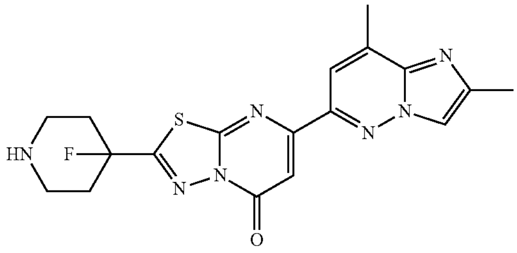

7-(2,8-dimethylimidazo[1,2-b]pyridazin-6-yl)-2-(4-fluoro-4-piperidyl)-[1,3,4]thiadiazolo[3,2-a]pyrimidin-5-one

9

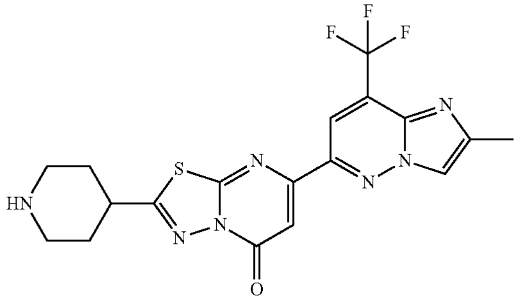 [SMILES: Cc1cn2nc(-c3cc(=O)n4nc(C5CCNCC5)sc4n3)cc(C(F)(F)F)c2n1]

7- [2-methyl-8-(trifluoromethyl)imidazo[1,2-b]pyridazin-6-yl]-2-(4-piperidyl)-[1,3,4]thiadiazolo[3,2-a]pyrimidin-5-one

10

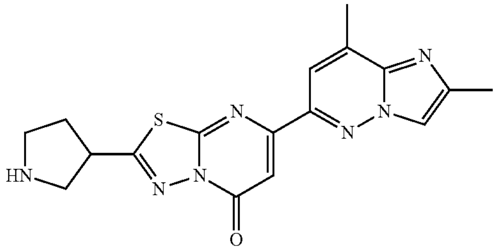 [SMILES: Cc1cn2nc(-c3cc(=O)n4nc(C5CCNC5)sc4n3)cc(C)c2n1]

7-(2,8-dimethylimidazo[1,2-b]pyridazin-6-yl)-2-pyrrolidin-3-yl-[1,3,4]thiadiazolo[3,2-a]pyrimidin-5-one or a pharmaceutically acceptable salt thereof.

13. The compound according to claim 1, selected from

2

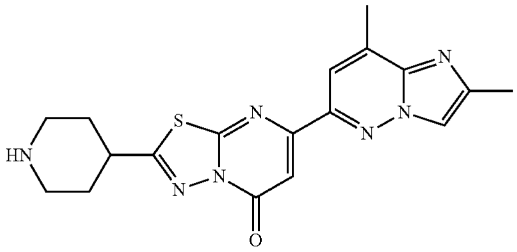

7-(2,8-dimethylimidazo[1,2-b]pyridazin-6-yl)-2-(4-piperidyl)-[1,3,4]thiadiazolo[3,2-a]pyrimidin-5-one

7

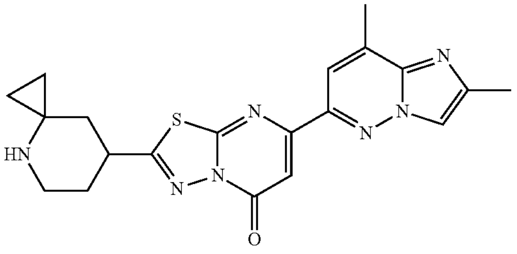

2-(4-azaspiro[2.5]octan-7-yl)-7-(2,8-dimethylimidazo[1,2-b]pyridazin-6-yl)-[1,3,4]thiadiazolo[3,2-a]pyrimidin-5-one

8

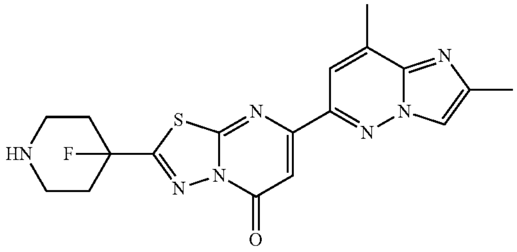

7-(2,8-dimethylimidazo[1,2-b]pyridazin-6-yl)-2-(4-fluoro-4-piperidyl)-[1,3,4]thiadiazolo[3,2-a]pyrimidin-5-one or a pharmaceutically acceptable salt thereof.

14. A pharmaceutical composition comprising a compound according to claim 1 and a therapeutically inert carrier.

15. A method of making a compound of Formula (I):

(I)

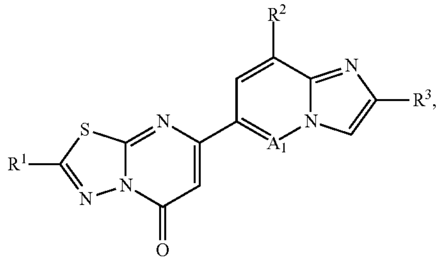

or a pharmaceutically acceptable salt thereof, wherein:

$A_1$ is —CH— or —N—;

$R^1$ is selected from hydrogen, $C_{1-8}$ alkyl, $C_{3-10}$ cycloalkyl, $C_{6-10}$ aryl, 5-12 membered heteroaryl, and 3-12 membered heterocycloalkyl, wherein each of said $C_{3-10}$ cycloalkyl, $C_{6-10}$ aryl, 5-12 membered heteroaryl, and 3-12 membered heterocycloalkyl is optionally substituted with one, two, three or four substituents independently selected from $R^4$;

$R^2$ is selected from hydrogen, halogen, cyano, amino, hydroxyl, $C_{1-8}$ alkyl, $C_{2-8}$ alkenyl, $C_1$-8 haloalkyl, $C_{1-8}$ alkoxy, $C_{1-8}$ haloalkoxy, and $C_{3-10}$ cycloalkyl;

$R^3$ is selected from hydrogen, halogen, $C_{1-8}$ alkyl, $C_{1-8}$ haloalkyl, and $C_{1-8}$ alkoxy; and $R^4$ is selected from halogen, $C_{1-8}$ alkyl, -12 membered heterocycloalkyl, 3-12 membered heterocycloalkyl-$C_{1-8}$ alkyl, $C_{1-8}$ alkyl-3-12 membered heterocycloalkyl, 3-12 membered haloheterocycloalkyl, $C_{3-10}$ cycloalkyl, $C_{3-10}$ cycloalkyl-$C_{1-8}$ alkyl, $C_{1-8}$ alkyl-$C_{3-10}$ cycloalkyl, $C_{3-10}$ halocycloalkyl, $C_{3-10}$ cycloalkyl-amino, $C_{6-10}$ aryl, $C_{6-10}$ aryl-$C_{1-8}$ alkyl, $C_{1-8}$ alkyl-$C_{6-10}$ aryl, $C_{6-10}$ haloaryl, cyano, hydroxy, oxo, $C_{1-8}$ haloalkyl, $C_{1-8}$ alkyl-carbonyl, $C_{1-8}$ alkoxy, $C_{1-8}$ haloalkoxy, $C_{1-8}$ alkoxy-$C_{1-8}$ alkyl, amino, $C_{1-8}$ alkylamino, di($C_{1-8}$ alkyl)amino, $C_{1-8}$ aminoalkyl, $C_{1-8}$ alkylamino-$C_{1-8}$ alkyl, di($C_{1-8}$ alkyl)amino-$C_{1-8}$ alkyl, $C_{1-8}$ aminoalkyl-amino, $C_{1-8}$ alkoxy-$C_{1-8}$ alkylamino, $C_{1-8}$ alkyl-carbonyl-amino, $C_{1-8}$ alkoxy-carbonyl-amino, $C_{1-8}$ hydroxy-alkyl, $C_{1-8}$ hydroxyalkoxy-$C_{1-8}$ alkyl, and $C_{1-8}$ hydroxyalkyl-amino;

the method comprising at least one step selected from:

(a) reacting a compound of formula (B1)

(B1)

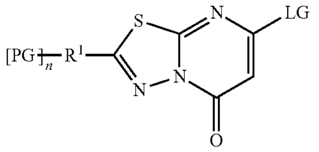

wherein:

n is 0 or 1;

PG is a protecting group;

LG is a suitable leaving group; and $R^1$ in formula (B1) is as defined for formula (I);

with a compound of formula (B2):

(B2)

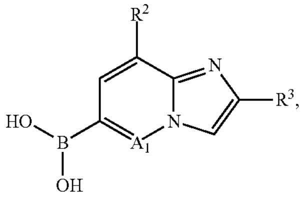

wherein:

$A_1$, $R^2$, and $R^3$ in formula (B2) are as defined for formula (I);

in a suitable solvent in the presence of a suitable base and a suitable palladium catalyst, to arrive at a compound of formula (B3):

(B3)

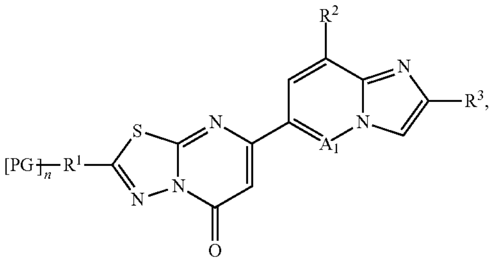

wherein:

PG and n are as defined for formula (B1); and $R^1$, $A_1$, $R^2$, and $R^3$ are as defined for formula (I); and (b) reacting the compound of formula (B3), wherein n is 1, in a suitable solvent and in presence of TMSI to yield the compound of formula (I).

* * * * *